United States Patent [19]

Muchowski

[11] 4,344,943
[45] Aug. 17, 1982

[54] 6-CHLORO- OR 6-BROMO-1,2-DIHYDRO-3H-PYRROLO[1,2-a]-PYRROLE-1-CARBOXYLIC ACIDS AND DERIVATIVES THEREOF

[75] Inventor: Joseph M. Muchowski, Sunnyvale, Calif.

[73] Assignee: Syntex (U.S.A.) Inc., Palo Alto, Calif.

[21] Appl. No.: 157,719

[22] Filed: Jun. 9, 1980

[51] Int. Cl.$^3$ ............ A61K 31/40; A61K 31/52; C07D 487/04; C07F 1/08
[52] U.S. Cl. ............ 424/245; 260/326.2; 260/326.22; 260/326.25; 260/326.31; 260/326.43; 424/253; 424/267; 424/274; 544/275; 546/200
[58] Field of Search ............ 260/326.25, 326.31, 260/326.22; 424/274, 245, 267, 253; 544/275; 546/200

[56] References Cited

U.S. PATENT DOCUMENTS

| | | | |
|---|---|---|---|
| 4,087,539 | 5/1978 | Muchowski et al. | 260/326.25 |
| 4,089,969 | 5/1978 | Muchowski et al. | 260/326.25 |
| 4,097,579 | 6/1978 | Muchowski et al. | 260/326.25 |
| 4,140,698 | 2/1979 | Van Horn et al. | 260/326.25 |
| 4,232,038 | 11/1980 | Kluge et al. | 260/326.25 |

*Primary Examiner*—Alton D. Rollins
*Attorney, Agent, or Firm*—Kate H. Murashige; Tom M. Moran; Alan M. Krubiner

[57] ABSTRACT

Novel 5-aroyl-6-chloro- or 6-bromo-1,2-dihydro-3H-pyrrolo[1,2-a]pyrrole-7-carboxylic acids represented by the formula

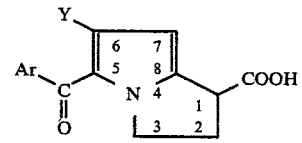

and the pharmaceutically acceptable, non-toxic esters and salts thereof, wherein Y is chloro or bromo and Ar is an optionally substituted phenyl, 2-furyl, or 2-thienyl ring or a 3-furyl, 3-thienyl, 2-pyrrolyl or 1-alkyl-2-pyrrolyl ring. These compounds are useful as anti-inflammatory, analgesic and antipyretic agents and as smooth muscle relaxants.

34 Claims, No Drawings

6-CHLORO- OR 6-BROMO-1,2-DIHYDRO-3H-PYRROLO[1,2-A]-PYRROLE-1-CARBOXYLIC ACIDS AND DERIVATIVES THEREOF

BACKGROUND OF THE INVENTION

1. Field of the Invention

This invention relates to (i) 5-aroyl-6-chloro-(or bromo)1,2-dihydro-3H-pyrrolo[1,2-a]pyrrole-1-caboxylic acids and the pharmaceutically acceptable, non-toxic alkyl esters and salts thereof; (ii) the use of these compounds as anti-inflammatory agents, analgesic agents, platelet aggregation inhibitors, fibrinolytic agents and smooth muscle relaxants (this includes both prophylactic and therapeutic use); (iii) pharmaceutical compositions comprising a compound of this invention and at least one pharmaceutical excipient; and (iv) processes for preparing the compounds of this invention.

2. Prior Art

Compounds are known which are represented by the formula

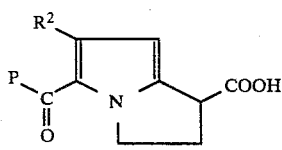

wherein P is a moiety selected from the group consisting of

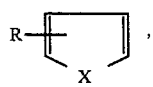 (IA)

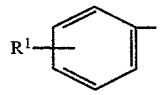 (IB)

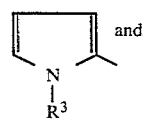 (IC)

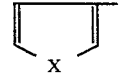 (ID)

in which
X is oxygen or sulfur,
R is hydrogen, methyl, chloro or bromo, the R substitution being at the 3, 4 or 5 positions of the thiophene ring,
$R^1$ is hydrogen, a lower alkyl group having 1 to 4 carbon atoms, a lower alkoxy group having from 1 to 4 carbon atoms, chloro, fluoro or bromo, the $R^1$ substitution being at the ortho, meta or para positions of the phenyl group, and
$R^2$ and $R^3$ are each independently hydrogen or a lower alkyl group having from 1 to 4 carbon atoms.

The compounds represented by Formula (IA) and (ID) are disclosed in U.S. Pat. No. 4,087,539, issued May 2, 1978 to Muchowski, et al while compounds of Formulas (IB) and (IC) are disclosed in U.S. Pat. No. 4,089,969, issued May 16, 1978 to Muchowski et al and U.S. Pat. No. 4,097,579 issued June 27, 1978 to Muchowski et al, respectively.

Compounds of Formula (IB) wherein $R^1$ is methylthio are disclosed in copending U.S. application Ser. No. 71,444 filed Aug. 31, 1979, now abandoned and compounds wherein $R^1$ is methylsulfinyl or methylsulfonyl are disclosed in U.S. Pat. No. 4,232,038, issued Nov. 4, 1980. All of these compounds are useful as antiinflammatory agents, analgesic agents, platelet aggregation inhibitors, fibrinolytic agents and smooth muscle relaxants. They can be used both prophylactically and therapeutically.

SUMMARY AND FURTHER DISCUSSION

The novel compounds of this invention are represented by the formula

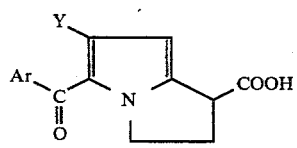 (A)

and the pharmaceutically acceptable, non-toxic esters having from 1 to 12 carbon atoms and salts thereof, wherein
Y is chloro or bromo and
Ar is a radical represented by the formula

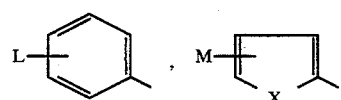

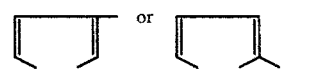

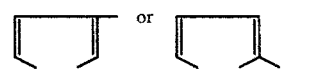

in which
X is sulfur or oxygen;
L is hydrogen, alkyl containing 1 to 4 carbon atoms, alkoxy containing 1 to 4 carbon atoms, Br, Cl, F, $CF_3$, CN or $S(O)_nR_3$
wherein $R_3$ is alkyl of 1 to 4 carbon atoms and n is 0, 1 or 2;
M is hydrogen, methyl, Cl or Br; and
Q is hydrogen or alkyl containing 1 to 4 carbon atoms.

In the compounds having the grouping

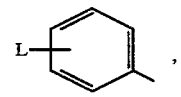

L can be in the ortho-, meta- or para-position.
In the compounds having the grouping

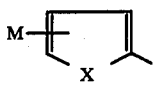

M can be at the 3-, 4- or 5-position of the ring.

The preferred compounds of this invention include those represented by Formula (A) wherein Ar is

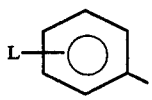

Y is chloro and L is methoxy, methylthio, chloro or fluoro. Of these, the compounds particularly preferred are the compounds where Y is chloro and L is chloro or fluoro.

The compounds of the present invention as described above and more fully below exhibit anti-inflammatory, analgesic and anti-pyretic activities and thus are useful in the treatment of inflammation, pain and/or pyrexia in mammals, as described hereinafter in detail. They are also smooth muscle relaxants and platelet aggregation inhibitors.

DEFINITIONS

The term "pharmaceutically acceptable, non-toxic esters and salts" as used herein refers to "alkyl esters" derived from hydrocarbons of branched or straight chain having from one to twelve carbon atoms and salts derived from inorganic and organic bases, respectively.

Typical pharmaceutically acceptable, non-toxic alkyl ester groups are, for example, methyl, ethyl, propyl, isopropyl, butyl, t-butyl, isoamyl, pentyl, isopentyl, hexyl, octyl, nonyl, isodecyl, 6-methyldecyl and dodecyl esters.

Pharmaceutically acceptable, non-toxic salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

Typical alkyl groups containing one to four carbon atoms are methyl, ethyl, propyl, isopropyl, butyl and the like. Typical alkoxy groups containing one to four carbon atoms include methoxy, ethoxy, propoxy, isopropoxy, butoxy and the like.

The compounds of this invention are named as 1-carboxylic acids using the numbering system set forth in the "Abstract of the Disclosure." For example in Formula A, where Ar is phenyl, L is hydrogen and Y is chloro, the name is 5-benzoyl-6-chloro-1,2-dihydro-3H-pyrrolo[1,2-a]-pyrrole-1-carboxylic acid. The methyl ester of that compound is named methyl 5-benzoyl-6-chloro-1,2-dihydro-2H-pyrrolo[1,2-a]pyrrole-1-carboxylate.

PROCESS OF PREPARATION

The novel compounds of the present invention are prepared by a process illustrated by Reaction Sequence 1 as follows:

REACTION SEQUENCE 1

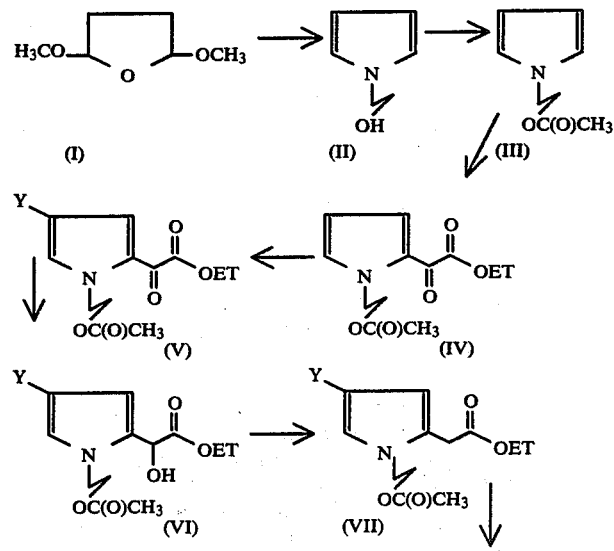

REACTION SEQUENCE 1

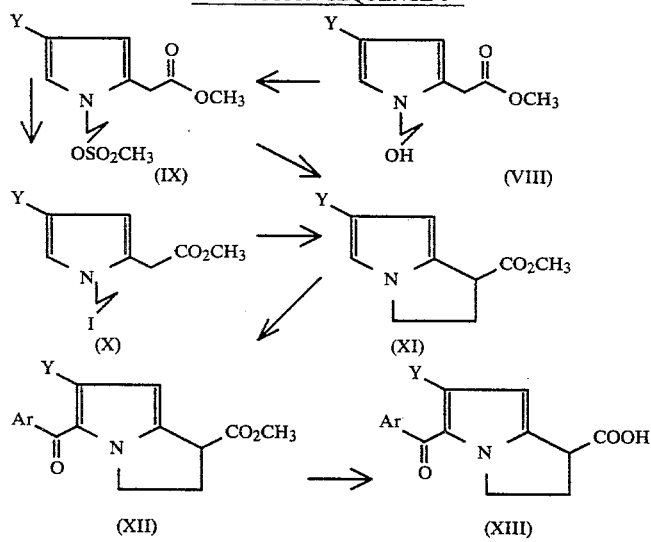

In practicing the process outlined above, in the first step in the preparation of the compound represented by Formula II, 2,5-dimethoxytetrahydrofuran (I) is reacted with ethanolamine in an organic acid. Generally the reaction is carried out with a 2 to about 10 times molar access of the ethanolamine over the dimethoxytetrahydrofuran with the reaction taking place in a substantial excess of the organic acid, preferably acetic acid. The reaction will take place at a temperature of about 50° to 125° C., preferably at about 110° to 120° C. or the boiling point of the reaction mixture. The reaction is completed within 5 to about 20 hours and generally will be completed in less than 10 hours at temperatures between 115° and 120° C. The reaction can be carried out in a continuous or a batch mode, preferably the latter.

Once the 1-(2-hydroxyethyl)pyrrole is obtained, it is esterified by any suitable means known in the art. Suitably, acetic acid is reacted with the 1-(2-hydroxyethyl)-pyrrole in the presence of a strong acid such as sulfuric acid and heating the reaction mixture sufficiently to distill off the water that is formed as a result of the reaction. Preferably however, the pyrrole is reacted with acetyl chloride or acetic anhydride in a suitable solvent wherein there is a molar excess of the acetyl chloride or acetic anhydride. The reaction takes place at room temperature and will be completed in a relatively short period of time, with only an hour or two at the most being required for the reaction to reach completion. The 1-(2-acetoxyethyl)pyrrole is then isolated and purified by any means known in the art such as extraction with a suitable organic solvent and removal of the solvent to yield the desired compound represented by Formula (III).

In the next step, a solution of pyridine in anhydrous dichloromethane is added to a stirred and cooled solution of ethoxalyl chloride in anhydrous dichloromethane so that the reaction temperature remains at about −20° to −25° C. Upon completion of this addition an approximately equimolar amount of 1-(2-acetoxyethyl)-pyrrole of Formula (III) in anhydrous dichloromethane is added while the temperature is maintained at temperatures of about 0° to −20° C. Washing with water, drying, removal of the solvent and purification gives ethyl 1-(2-acetoxyethyl)pyrrole-2-glyoxylate.

Once the glyoxylate of Formula (IV) is obtained, it is chlorinated or brominated using a suitable chlorinating or brominating agent. To increase selectivity, the reaction is effected at low temperatures. Thus, the glyoxylate of Formula (IV) is cooled to 50° C. and preferably about −70° C. after dissolving in an inert, anhydrous halogenated alkane solvent such as dichloromethane. A suitable chlorinating agent is sulfuryl chloride while a suitable brominating agent is bromine. The reaction mixture, after the addition of the chlorinating or brominating agent is complete, is allowed to warm up to ambient temperature, whereupon the organic solvent is removed. Generally, the reaction takes no longer to complete than it takes to add the chlorinating or brominating agent. The 4-chloro or 4-bromopyrrole thus formed is readily separated from other related compounds by suitable means known in the art such as thin layer chromatography, column chromatography, gas-liquid chromatography (GLC) or high pressure liquid chromatography (HPLC).

The 4-chloro or 4-bromoglyoxylate of Formula (V) is then reduced to the corresponding ethyl 1-(2-acetoxyethyl)-pyrrole-2-glycolate. This selective reduction of the 1-keto group is achieved by using a reducing agent such as an alkali metal borohydride (for example potassium borohydride or, preferably sodium borohydride) in a methanol/water solution. The reaction takes place at temperatures of −10° to about −60° C., preferably about −30° C. for the 4-chloro compound and −50° C. where Y is Br.

In the next step iodine is dissolved in a dry aromatic hydrocarbon solvent, such as benzene, and triphenylphosphene is added in an inert atmosphere (e.g. argon). The α-hydroxyacetate is then added to this mixture and reacted for a period of time sufficient to eliminate the 1-hydroxy group. Generally, for the 4-chloro compounds the reaction mixture will be reacted for less than about 5 hours and generally will take about 2½ hours at reflux temperatures. The resulting compound is then isolated using methods well known in the art.

The resulting compound of Formula (VII) is then converted to the corresponding methyl 1-(2-hydroxyethyl)-4-chloro or 4-bromopyrrole-2-acetate by dissolving the compound of Formula (VII) in anhydrous methanol and adding a suitable amount of 1,5-diazabicyclo[4.3.0]non-5-ene (DBN). Generally the reaction takes place at room temperature in an inert atmosphere (nitrogen) and is completed in less than about 20 hours, generally about 6 hours for the 4-chloro compound and about 18 hours for the 4-bromo compound. After suitable isolation and purification one then obtains a compound set forth as Formula (VIII), namely a methyl 1-(2-hydroxyethyl)-4-chloro or 4-bromopyrrole-2-acetate.

Esterification of the compound represented by Formula (VIII) with methanesulfonyl chloride in the presence of a tertiary amine, i.e., triethylamine, pyridine and the like, optionally in the presence of a cosolvent such as dichloromethane, at a temperature of from about −10° C. to about room temperature, for about 10 minutes to about 2 hours produces the corresponding mesylate of Formula (IX). This in turn, is converted into the corresponding N-(3-iodoethyl)pyrrole of Formula (X) by reaction with sodium iodide in acetonitrile solution, at reflux temperature for from about one to about ten hours.

Upon reaction of the iodoethylpyrrole of Formula (X) with sodium hydride in a suitable inert organic solvent such as dimethylformamide there is obtained methyl-1,2-dihydro-3H-6-chloro or 6-bromopyrrolo[1,2-a]pyrrole-1-carboxylate. This cyclization is conducted under an inert atmosphere, i.e., under argon or nitrogen atmosphere, at temperatures of the order of from about 15° to about 40° C., for a period of time of from about 15 minutes to about 4 hours. Best results are obtained conducting the reaction at room temperature, for about 30 minutes.

Alternatively, the compounds of Formula (VII) can be prepared by direct cyclization of the mesylate (V), with sodium hydride in dimethylformamide solution, at from about −10° C. to about room temperature, for from about 30 minutes to about 2 hours.

Condensation of a compound of Formula (XI) with an amide of the formula

wherein Ar has the above-indicated meaning, affords the corresponding methyl 5-aroyl-1,2-dihydro-3H-6-chloro or 6-bromopyrrolo[1,2-a]pyrrole-1-carboxylate of Formula (XII). This reaction is conducted in an inert organic aprotic solvent and in the presence of phosphorous oxychloride, at reflux temperature for from about 1 to about 175 hours, under an inert atmosphere, followed by further reflux in the presence of sodium acetate, for from about 2 to about 10 hours. Alternatively, instead of phosphorous oxychloride other acid chlorides such as phosgene or oxalyl chloride may be used.

In the preferred embodiments, this condensation is carried out by adding a solution of compound (X) in a suitable solvent to a previously refluxed mixture of 1.1 to 5 molar equivalents of both the desired amide and phosphorous oxychloride in the same solvent, refluxing the reaction mixture thus obtained for from about 6 to about 72 hours under an argon atmosphere and thereafter adding thereto from about 3 to about 10 molar equivalents of sodium acetate, followed by an additional reflux period for from about 4 to about 6 hours.

Adequate solvents for this reaction are the halogenated hydrocarbons such as dichloromethane, 1,2-dichloroethane, chloroform, carbon tetrachloride and the like, dimethoxyethane and tetrahydrofuran. The preferred solvent 1,2-dichloroethane.

Representative of the N,N-dimethyl arylamides which can be used are:

N,N-dimethylbenzamide;
N,N-dimethyl-o-toluamide;
N,N-dimethyl-m-toluamide;
N,N-dimethyl-p-toluamide;
N,N-dimethyl-p-ethylbenzamide;
N,N-dimethyl-o-propylbenzamide;
N,N-dimethyl-m-butylbenzamide;
N,N-dimethyl-o-methoxybenzamide;
N,N-dimethyl-m-methoxybenzamide;
N,N-dimethyl-p-ethoxybenzamide;
N,N-dimethyl-p-isopropoxybenzamide;
N,N-dimethyl-p-butoxybenzamide;
N,N-dimethyl-o-chlorobenzamide;
N,N-dimethyl-m-chlorobenzamide;
N,N-dimethyl-p-chlorobenzamide;
N,N-dimethyl-o-fluorobenzamide;
N,N-dimethyl-p-fluorobenzamide;
N,N-dimethyl-m-bromobenzamide;
N,N-dimethyl-p-bromobenzamide;
N,N-dimethyl-p-trifluoromethylbenzamide;
N,N-dimethyl-p-cyanobenzamide;
N,N-dimethyl-p-methylthiobenzamide;
N,N-dimethyl-m-ethylthiobenzamide;
N,N-dimethyl-p-propylthiobenzamide;
N,N-dimethyl-o-methylsulfinylbenzamide;
N,N-dimethyl-m-ethylsulfinylbenzamide;
N,N-dimethyl-p-butylsulfinylbenzamide;
N,N-dimethyl-o-ethylsulfonylbenzamide;
N,N-dimethyl-m-methylsulfonylbenzamide;
N,N-dimethyl-p-isopropylsulfonylbenzamide;
N,N-dimethylthiophene-2-carboxamide,
N,N-dimethylfuran-2-carboxamide,
N,N-dimethyl-3-methylthiophene-2-carboxamide,
N,N-dimethyl-4-methylthiophene-2-carboxamide,
N,N-dimethyl-5-methylthiophene-2-carboxamide,
N,N-dimethyl-4-chlorothiophene-2-carboxamide,
N,N-dimethyl-5-chlorothiophene-2-carboxamide,
N,N-dimethyl-3-bromothiophene-2-carboxamide,
N,N-dimethyl-5-bromothiophene-2-carboxamide,
N,N-dimethyl-3-methylfuran-2-carboxamide,
N,N-dimethyl-4-methylfuran-2-carboxamide,
N,N-dimethyl-4-chlorofuran-2-carboxamide,
N,N-dimethyl-5-chlorofuran-2-carboxamide,
N,N-dimethyl-4-bromofuran-2-carboxamide,
N,N-dimethyl-5-bromofuran-2-carboxamide,
N,N-dimethylthiophene-3-carboxamide and
N,N-dimethylfuran-3-carboxamide.
N,N-dimethylpyrrole-2-carboxamide,
N,N-dimethyl-1-methylpyrrole-2-carboxamide,
N,N-dimethyl-1-ethylpyrrole-2-carboxamide,
N,N-dimethyl-1-propylpyrrole-2-carboxamide and
N,N-dimethyl-1-butylpyrrole-2-carboxamide.

These amides are known, commercially available compounds or can be prepared in a conventional manner from the corresponding acids, i.e., by conversion into the acid chlorides followed by treatment with dimethylamine.

Alternatively a compound represented by Formula (XII) may be prepared by condensing a compound of Formula (XI) with an acid chloride of the formula

wherein Ar has the above-indicated meaning. This reaction is carried out in an inert atmosphere (e.g. argon) and a suitable inert hydrocarbon solvent such as xylene. Suitable acid chlorides include those which correspond to N,N-dimethylarylamides set forth hereinbefore and include:

benzoyl chloride;
o-toluoyl chloride;
m-toluoyl chloride;
p-toluoyl chloride;
p-ethylbenzoyl chloride;
o-propylbenzoyl chloride;
m-butylbenzoyl chloride;
o-methoxybenzoyl chloride;
m-methoxybenzoyl chloride;
p-ethoxybenzoyl chloride;
p-isopropoxybenzoyl chloride;
p-butoxybenzoyl chloride;
o-chlorobenzoyl chloride;
m-chlorobenzoyl chloride;
p-chlorobenzoyl chloride;
o-fluorobenzoyl chloride;
p-fluorobenzoyl chloride;
m-bromobenzoyl chloride;
p-bromobenzoyl chloride;
p-trifluoromethylbenzoyl chloride;
p-cyanobenzoyl chloride;
p-methylthiobenzoyl chloride;
m-ethylthiobenzoyl chloride;
p-propylthiobenzoyl chloride;
o-methylsulfinylbenzoyl chloride;
m-ethylsulfinylbenzoyl chloride;
p-butylsulfinylbenzoyl chloride;
o-ethylsulfonylbenzoyl chloride;
m-methylsulfonylbenzoyl chloride;
p-isopropylsulfonylbenzoyl chloride;
thiophene-2-carbonyl chloride,
furan-2-carbonyl chloride,
3-methylthiophene-2-carbonyl chloride,
4-methylthiophene-2-carbonyl chloride,
5-methylthiophene-2-carbonyl chloride,
4-chlorothiophene-2-carbonyl chloride,
5-chlorothiophene-2-carbonyl chloride,
3-bromothiophene-2-carbonyl chloride,
5-bromothiophene-2-carbonyl chloride,
3-methylfuran-2-carbonyl chloride,
4-methylfuran-2-carbonyl chloride,
4-chlorofuran-2-carbonyl chloride,
5-chlorofuran-2-carbonyl chloride,
4-bromofuran-2-carbonyl chloride,
5-bromofuran-2-carbonyl chloride,
thiophene-3-carbonyl chloride and
furan-3-carbonyl chloride.
pyrrole-2-carbonyl chloride,
1-methylpyrrole-2-carbonyl chloride,
1-ethylpyrrole-2-carbonyl chloride,
1-propylpyrrole-2-carbonyl chloride and
1-butylpyrrole-2-carbonyl chloride.

These acid chlorides are known, commercially available compounds or can be prepared in a conventional manner from the corresponding acids.

Upon alkaline hydrolysis of the methyl ester group in a compound of Formula (XII) there is obtained the corresponding free acid of Formula (XIII). This hydrolysis is effected in a conventional manner, with an alkali metal hydroxide or alkali metal carbonate, e.g., sodium hydroxide, potassium hydroxide, sodium carbonate, potassium carbonate and the like, in an aqueous lower aliphatic alcohol, e.g., methanol, ethanol and the like, at a temperature of from about room temperature to reflux, for from about 15 minutes to about 2 hours, under an inert atmosphere. Preferably, this hydrolysis is effected with aqueous methanolic potassium carbonate, at reflux temperature for about 30 minutes.

It is to be understood that isolation of the compounds described herein can be effected, if desired, by any suitable separation or purification procedure, such as, for example, extraction, filtration, evaporation, distillation, crystallization, thin-layer chromatography or column chromatography, high pressure liquid chromatography (HPLC) or a combination of these procedures. Illustrations of suitable separation and isolation procedures for other compounds are available in the art. For example, see U.S. Pat. Nos. 4,087,539; 4,089,969; and 4,097,579. However, other equivalent separation or isolation procedures could, of course, also be used.

An alternative route for the preparation of 5-alkylsulfinyl- and 5-alkylsulfonylbenzoyl-6-chloro- or 6-bromo-1,2-dihydro-3H-pyrrolo[1,2-a]pyrrole-1-carboxylic acids is set forth in Reaction Sequence 2.

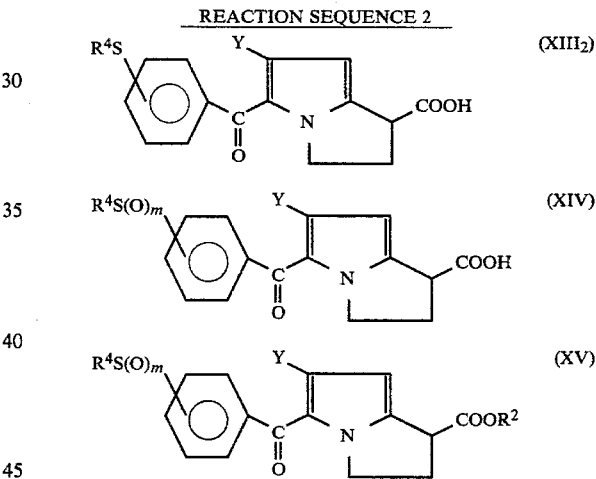

In this reaction sequence, the 5-alkylthiobenzoyl-6-chloro- or 6-bromo-1,2-dihydro-3H-pyrrolo[1,2-a]pyrrole-1-carboxylic acids prepared in accordance with the method discussed for Reaction Sequence 1 is converted to the corresponding alkylsulfinylbenzoyl compound or the alkylsulfonylbenzoyl compound by a suitable oxidation method. For example, the 5-alkylthiobenzoyl compound can be converted to the corresponding 5-alkylsulfinylbenzoyl compound by treatment with an appropriate oxidizing agent at low temperatures of at about −10° to about 20°, preferably about 0° C. Suitable oxidizing agents include sodium periodate, m-chloroperbenzoic acid, ceric ammonium nitrate, hydrogen peroxide containing selenium dioxide, and the like. Generally, a molar quantity of the oxidizing agent which is equal to the molar quantity of the alkylthiobenzoyl compound is employed. Usually the reaction is completed within 24 hours.

To convert the 5-alkylthiobenzoyl compound to the corresponding 5-alkylsulfonylbenzoyl compound oxidizing agents are employed such as m-chloroperbenzoic acid, perphthalic acid, peracetic acid, and the like. This reaction takes place at a temperature of about −10 to about +10, preferably about −5° to about 0° C. In general, a molar quantity of the oxidizing agent which is equal to at least twice the molar quantity of the 5-alkylthiobenzoyl compound is used.

It is to be understood that isolation of the 5-alkylsulfinyl and 5-alkylsulfonyl compounds described herein can also be effected, if desired, by any suitable separation or purification procedure, such as, for example, extraction, filtration, evaporation, distillation, crystallization, thin-layer chromatography or column chromatography, high pressure liquid chromatography (HPLC) or a combination of these procedures. Illustrations of suitable separation and isolation procedures for other compounds are available in the art. For example, see U.S. Pat. Nos. 4,087,539; 4,089,969; and 4,097,579. However, other equivalent separation or isolation procedures could, of course, also be used.

UTILITY AND ADMINISTRATION

The compounds of Formula (A) where Y and Ar are as defined hereinbefore and the pharmaceutically acceptable non-toxic esters and salts thereof, are useful as anti-inflammatory agents, analgetic agents, antipyretic agent, vasospasm inhibitors (e.g., vs migraine) platelet aggregation inhibitors, fibrinolytic agents, and as smooth muscle relaxants (e.g., for treatment of dysmenorrhea). These compounds can be used both prophylactically and therapeutically.

The compositions containing these compounds are thus useful in the treatment and elimination of inflammation and/or pain. Thus, inflammatory conditions of the musculo-skeletal system, skeletal joints and other tissues are treated, such as the treatment of inflammatory conditions including but not limited to rheumatism, contusion, laceration, arthritis, bone fractures, post-traumatic conditions, inflammation associated with bacterial infections, and gout. The preferred compounds show anti-inflammatory activity which is superior to certain related compounds known in the art. Further, those particularly preferred compounds show even greater anti-inflammatory activity as compared with related compounds known in the art. In those cases in which the inflammatory conditions include pain and pyrexia coupled with the inflammation, the instant compounds are useful for the relief of these conditions as well as the inflammation. The compounds are also useful for treating pain which is not necessarily associated with inflammation, e.g., migraine, post-surgical pain, etc.

Initial small animal screening tests to determine anti-inflammatory activity potential include the carrageenin induced paw inflammation in the rat according to the method of Winter, et al (Proc Soc Exp Biol Med 111:544–547, 1962) and the cotton pellet granuloma test in the rat according to the method of Meier, et al (Experientia 6:469–471,1950) and modifications thereof.

In addition, in certain cases, the anti-inflammatory activity may be evaluated by using the adjuvant arthritis assay according to the method of Pearson (Proc Soc Exp Biol Med 91:95–101, 1956). Also, in vitro tests, for example those using synovial explants from patients with rheumatoid arthritis, Dayer et al (J Exp Med 145:1399–1404, 1977), are useful in determining whether compounds exhibit anti-inflammatory activity.

Small animal screening tests to determine analgetic activity potential include the mouse analgetic (anti-writing) assay according to the method of Hendershot and Forsaith (J Pharmacal Exp Ther 125:237–240, 1959).

Generally, the antipyretic activity potential is indicated by the anti-inflammatory potential as measured by the previously mentioned assays.

Platelet aggregation inhibition potential is determined by using turbidimetric method of Born (J Physiol (Lond) 162:67–68p, 1962).

Potential activity as a smooth muscle relaxant is determined in vitro using the method of Vickery (Prostoglandins Med 2:299–315, 1979) or Vickery (Prostaglandins Med 2:225–235, 1979).

Administration of the active compounds of Formula (A) where Y and Ar are as defined hereinbefore and the pharmaceutically acceptable, non-toxic esters and salts thereof, in an appropriate pharmaceutical composition can be via any of the accepted modes of administration of agents for the treatment of inflammation, pain or pyrexia, or the prophylaxis thereof. Thus, administration can be for example, orally, parenterally or topically, in the form of solid, semi-solid or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of Formula (A) and the pharmaceutically acceptable, non-toxic esters and salts thereof, and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 0.02 to 20 mg/kg of body weight per day of the active compound of Formula (A) and the pharmaceutically acceptable, non-toxic esters and salts thereof is used. Most conditions respond to treatment comprising a dosage level of the order of 0.05 to 2 mg. per kilogram of body weight per day. Thus, for administration to a 70 kg person, the dosage range per day would be about 1.4 to 1400 mg per day, preferably about 3.5 to 140 mg per day.

For such oral administration, a pharmaceutically acceptable, non-toxic composition is formed by the incorporation of any of the normally employed excipients, such as, for example, pharmaceutical grades of mannitol, lactose, starch, magnesium stearate, sodium saccarine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

Generally, the pharmaceutically acceptable compositions will contain about 1% to about 90% by weight of the pharmaceutically active compound of this invention and 99% to 10% by weight of suitable pharmaceutical excipients. Preferably, the composition will be about 3.5 to 60% by weight of a pharmaceutically active compound, with the rest being suitable pharmaceutical excipients.

The active compounds of Formulas (A) and the pharmaceutically acceptable, non-toxic esters and salts thereof, may be formulated into a suppository using, for example, polyethylene glycols (PEG), for example, PEG 1000 (96%) and PEG 4000 (4%), as the carrier. Liquid pharmaceutically administerable compositions can, for example, be prepared by dissolving, dispersing, etc. an active compound, as described above, and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pa. 14th. Edition, 1970. The composition to be administered will, in any event, contain a quantity of the active compound(s) in a pharmaceutically effective amount for relief of the particular condition being treated in accordance with the teachings of this invention.

The compounds of Formula (A) and the non-toxic, pharmaceutically acceptable, esters and salts thereof, described above, are also uterine smooth muscle relaxants and thus are useful as agents for maintaining the pregnancy of pregnant mammals, for the benefit of the mother and/or fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formulas (A) and the pharmaceutically acceptable, non-toxic esters and salts thereof, are used as agents for delaying the onset of, or for postponing, parturition. As used in this application, the phrase "to delay the onset of parturition" is intended to cover that delay in parturition caused by the administration of the compounds of Formulas (A) and the pharmaceutically acceptable, non-toxic esters and salts thereof, at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the preganancy when the fetus is considered to be "yiable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formula (A) and the pharmaceutically acceptable, non-toxic esters and salts thereof after uterine muscle contractions have begun. The condition of the patient, including the time within the gestation period when the contractions have begun, the severity of the contractions and how long the contractions have taken place will affect the results achieved with the administration of the compounds hereof. For example, the effect can be to reduce the intensity and/or the duration of the contractions (the actual act of parturition being "prolonged"), or to stop the contractions altogether. In either case, the effect will be to prolong the gestation period although, depending upon the conditions of the patient as described above, the effect may either by slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formula (A) and the pharmaceutically acceptable, non-toxic esters and salts thereof, as a uterine smooth muscle relaxant as set forth herein should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formula (A) and the pharmaceutically acceptable, non-toxic esters and salts thereof, or a pharmaceutical composition containing same, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, gelatin, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution of suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 14th Edition, 1970. The composition or formulation to be administered will, in any event, contain a quantity of the active compound(s) in an amount effective to delay the onset of parturition or to postpone parturition if uterine contractions have already begun. Generally a daily dose of from 0.5 mg. to about 25 mg. of the active compound per kilogram of body weight will be administered, with administration being a single daily dose or up to three or four smaller dosages regularly given throughout the day. The amount of active compound administered will, of course, depend on its relative activity.

The following Preparations and Examples illustrate the invention but are not intended to limit its scope. The abbreviation t.l.c. refers to thin-layer chromatography and all mixture ratios used with regard to liquids refer to volume ratios. Also where necessary, examples are repeated to prepare additional material for subsequent examples; and unless otherwise specified the reactions are carried out at room temperature (20° C. to 30° C.).

In the following Preparations and Examples, the parenthetical references are to the Formulas of Reaction Sequences 1 or 2 or Formulas A, $A_2$, $A_3$ or $A_4$, as appropriate. The Preparations and Examples are given as representative of the compounds of this invention but are not intended to be limited thereto.

PREPARATION I

Ethyl 1-(2-acetoxyethyl)pyrrole-2-glyoxalate

Acetic acid (32.2 k.) is charged to a reactor, and 26.1 kg of ethanolamine is charged over a 1 hour period, keeping the temperature below 54°, thereto. The resulting mixture is cooled to 28° C., 2,5-dimethoxytetrahydrofuran (12.5 k.) is charged to the reactor, and the contents are heated at 115°–119° for 8 hours, then cooled to 20°. The mixture is diluted with saturated sodium chloride solution (80 l.) and water (54 l.) and extracted with two 80 l. volumes of ethylacetate. The extracts are washed with 80 l. saturated sodium chloride solution, 80 l. saturated sodium bicarbonate solution and twice with 80 l. saturated sodium chloride solution. The organic layers are dried with 5 lbs. sodium sulfate and evaporated in vacuo to 40 l. This solution is treated with 13.5 kg. silica gel and 40 l. hexane for 15 minutes. The silica gel is removed by filtration and washed with 80 l. 1:1 ethylacetate/hexane, then with 5 l. of the same solvent mixture. The filtrate and washings are evaporated to near dryness in vacuo. The residue is dissolved in 10 l. methanol and evaporated to dryness. This methanol evaporation is then repeated. The residue is dissolved in 40 l. methanol and 39.65 g. of sodium is added to the solution. This solution is heated at reflux temperature for 45 minutes and then cooled to 20°. Acetic acid (98.5 mls.) is added to the solution. The resulting solution is evaporated to dryness to afford 1-(2-hydroxyethyl)pyrrole (Formula II).

The resulting product is reacted with acetic anhydride in accordance with the method of F. F. Blicheand E. S. Blake, J.Am.Chem.Soc.,53, 1015 (1931). A mixture of 1-(2-hydroxyethyl)pyrrole (147 g, 1.32 mole), pyridine (415 ml) and acetic anhydride (139 ml) is heated on a steam bath for 0.5 hours. The reaction mixture is cooled to room temperature, poured into water (one l) and the product is extracted into ethyl acetate (3×1 l). The extract is washed successively with dilute hydrochloric acid, saturated sodium chloride solution, dilute sodium bicarbonate solution, and again with saturated sodium chloride solution. The extract is dried over sodium sulfate, evaporated in vacuo and the residue (150 g) is subjected to column chromatography on Florisil ® activated magnesium silicate. The desired product is eluted with hexane-dichloromethane (1:1) to give 128 g (55%) 1-(2-acetoxyethyl)pyrrole, an oil, identical to an authentic specimen.

A solution of pyridine (89 ml) in anhydrous dichloromethane (2 l) is added to a stirred and cooled solution of ethoxalyl chloride (136 g, 1 mole) in dry dichloromethane (2 l) at a rate such that the reaction temperature is maintained at −20° to −25° C. Upon completion of this addition, a solution of 1-(2-acetoxyethyl)pyrrole (128 g, 0.84 mole) in dry dichloromethane (2 l) is added at a rate such that the reaction temperature is maintained at −20° to −0° C. The reaction mixture is then stirred at −20° to 0° C. for 2 hours and at ambient temperature for 16 hours. The reaction mixture is then washed successively with dilute hydrochloric acid, dilute sodium bicarbonate solution and water. The organic phase is dried over sodium sulfate and evaporated in vacuo to give 211 g of an oily residue which is subjected to column chromatography on Florisil ® activated magnesium silicate. The product is eluted with hexane-ethyl acetate (first 19:1 then 4:1) to give (151 g, 71%) ethyl 1-(2-acetoxyethyl)pyrrole-2-glyoxalate as an oil having the following physical characteristics:

U.V.: 208 sh, 245, 311 mm (E 2820, 4170, 11,800).
I.R.: (CHCl$_3$); 1740, 1665 cm$^{-1}$.
M.S.: 253 (M+).

PREPARATION II

Ethyl 1-(2-acetoxyethyl)-4-chloropyrrole-2-glyoxalate

A. The resulting ethyl 1-(2-acetoxyethyl)pyrrole-2-glyoxalate prepared as in Preparation I (40.5 g, 0.16 mol.) is dissolved in anhydrous dichloromethane (900 ml.) and cooled to −70°. Recently distilled sulfuryl chloride (13.7 ml., 0.17 mol.) is added in a dropwise manner. When the addition is completed, the solution is allowed to come to room temperature spontaneously. After two hours at this temperature TLC (silica gel; hexane:ethyl acetate; 80:20) shows the absence of starting material. The solvent is removed in vacuo and the oily residue is dissolved in dichloromethane (300 ml.) and washed to neutrality with water. The organic phase is dried over sodium sulfate and evaporated to dryness in vacuo. The residue, which weighed 63 g. is purified by column chromatography on silica gel (800 g.) using hexane ethyl acetate (90:10) as the eluting solvent. This procedure yields 19 g. (41% yield) of ethyl 1-(2-acetoxyethyl)4-chloropyrrole-2-glyoxalate (Formula V where Y is Cl) having the following physical constants:

U.V.: 275, 310 nm (ε5630, 9340).
I.R. 1743, 1654 cm$^{-1}$ (CHCl$_3$).

N.M.R.: (CDCl$_3$); 1.44 (t, 3H, J=7.2); 2.07 (s, 3H); 4.00 (s, 2H); 4.23–4.70 (m, 6H); 7.00 (d, J=1.8, 1H); 7.27 (d, J=1.8, 1H).

M.S.: 287 (M+).

Calcd. for C$_{12}$H$_{15}$ClNO$_5$: C, 50.09; H, 4.90; Cl, 12.32. Found: C, 50.12; H, 4.95; Cl, 12.35.

PREPARATION III

Ethyl 1-(2-acetoxyethyl)-4-bromopyrrole-2-glyoxalate

Three ml (58.3 mmole) of bromine is added in a dropwise manner to a stirred solution of 14.77 g (58.3 mmole) of ethyl 1-(2-acetoxyethyl)pyrrole-2-glyoxalate in 200 ml anhydrous dichloromethane, cooled to −75° C. After the addition, the reaction is left at −75° C. for 2.5 hours and then the temperature is allowed to increase to room temperature. The solvent is removed in vacuo, dichloromethane is added to the residue and the solution is washed successively with water, 10% sodium bicarbonate solution and water. The organic phase is dried over sodium sulfate, and the solvent is removed in vacuo. The crude product thus obtained (18.3 g) is subjected to column chromatography on Florisil (1 Kg) using hexane-ethyl acetate (9:1) as the eluting solvent. There is thus obtained upon removal of the solvent, 10.9 g (56%) of ethyl 1-(2-acetoxyethyl)-4-bromopyrrole-2-glyoxalate as an oil having the following physical constants:

U.V.: 270,310 nm ($\mu$5500,8910).

I.R.: (CHCl$_3$); 1736,1650 cm$^{-1}$.

N.M.R.: (CDCl$_3$); 1.41 (t, 3H, J=7.4); 2.03 (s, 3H); 4.20–4.70 (m, 6H); 7.00 (d, 1H, J=1.8); 7.33 (d, 1H, J=1.8).

M.S.: 331,333 (M+).

Calcd. for C$_{12}$H$_{14}$BrNO$_5$: C, 43,38; H, 4.24; Br, 24.06. Found: C, 43.33; H, 5.29; Br, 24.01.

PREPARATION IV

A. Ethyl 1-(2-acetoxyethyl)-4-chloropyrrol-2-acetate

A solution of water (25 ml.) in methanol (300 ml.) is cooled in a dry ice:carbon tetrachloride:acetone bath to −30° and 23.7 g. of sodium borohydride is added thereto. When the violent reaction has subsided, there is added, in a drop wise manner, 40 g. (0.139 mol.) of ethyl 1-(2-acetoxyethyl)-4-chloropyrrole-2-glyoxalate dissolved in methanol (400 ml.) at a rate such that the temperature does not exceed −20°. The reaction is maintained at this temperature for two hours when there is added a solution of 21.5 ml. of acetic acid in 320 ml. water. The solution is stirred for a further 1 hour at −30° during which time a white precipitate forms. This solid is collected by filtration and dissolved in dichloromethane. The organic solution was washed with saturated sodium chloride solution, dried over sodium sulphate and evaporated in vacuo. There is obtained 33.15 g. of a solid product which is homogeneous by thin layer chromatography. Recrystallization from dichloromethane-hexane yields ethyl 1-(2-acetoxyethyl)-4-chloropyrrole-2-glycolate, m.p. 60°–61° C. (Formula VI where Y is Cl).

In an argon atmosphere, 27.9 g. (0.11 mol.) of iodine is dissolved in 400 ml. of dry benzene and 57.7 g. (0.22 mol.) of triphenylphosphine is added. After stirring for 5–10 minutes 32.0 g. (0.11 mol.) of the 1-hydroxyacetate is added all at once. The mixture is heated at reflux temperature for 2.5 hours. During this time triphenylphosphine oxide separated from solution. At the end of the reaction the mixture is cooled and the solids are separated by filtration. The filtrate is washed with 10% aqueous sodium bicarbonate solution and then with a saturated solution of sodium chloride in water. The solution is dried over sodium sulphate and evaporated to dryness in vacuo. The resulting dark colored oil is purified by column chromatography on Florisil® brand activated magnesium silicate using hexane-ethyl acetate (90:10) as the eluting solvent to give 26 g. (83% yield) of ethyl 1-(2-acetoxyethyl)-4-chloropyrrol-2-acetate (Formula VII where Y is Cl) having the following physical constants:

U.V.: 218 nm ($\epsilon$6460).

I.R.: 1736 cm$^{-1}$ (CHCl$_3$).

N.M.R.: (CDCl$_3$); 1.24 (t, 3H, J=7.1); 2.05 (s, 3H); 3.60 (s, 2H); 3.93–4.40 (m, 6H); 6.00 (d, 1H, J=1.8); 6.60 (d, 1H, J=1.8).

M.S.: 273 (M+).

Calcd. for C$_{12}$H$_{16}$ClNO$_4$: C, 52.65; H, 5.89; N, 5.11. Found: C, 52.57; H, 5.90; N, 5.09.

B. Ethyl 1-(2-acetoxyethyl)-4-bromopyrrol-2-acetate

Methanol (100 ml) containing 2.5 ml water is cooled to −50° C. and 3.07 g of sodium borohydride (81.2 mmole) is added with stirring. After 5 minutes, (8.9 g) (26.7 mmole) ethyl 1-(2-acetoxyethyl)-2-bromopyrrole-2-glyoxalate is dissolved in 40 ml methanol and added at a rate such that the reaction temperature does not exceed −40° C. After 1 hour at this temperature, 50% aqueous acetic acid is added until the solution is weakly acidic. The methanol is then removed in vacuo, 100 ml ethyl acetate is added to the residue, the organic phase is washed well with saturated salt solution, then dried over sodium sulfate. The solvent is removed in vacuo and the residue is immediately crystallized, at low temperature (Dry Ice-acetone bath), from ether. The ethyl 1-(2-acetoxyethyl)-4-bromo-2-glycolate thus obtained (6.0 g, 67%) exhibits a m.p. of 59° C. but is unstable and is be stored in an evacuated vessel at −10° C.

Triphenylphosphine (15.2 g, 58.0 mmole) is added to a solution of iodine (7.37 g, 29.0 mmole) in anhydrous benzene (300 ml) maintained in a nitrogen atmosphere. After agitation for 10 minutes, a solution of the ethyl glyoxalate (9.7 g, 29.0 mmole) in dry benzene (100 ml) is added all at once. The resultant is left at room temperature for 18 hours. The solid which precipitates is collected by filtration, washed well with ether, and the filtrate evaporated in vacuo. The residue is dissolved in dichloromethane, washed well with saturated salt solution, dried and evaporated. The material thus obtained is subjected to column chromatography on silica gel (400 g) using hexane-ethyl acetate (9:1 and then 4:1) to elute the product. A few drops of triethylamine is added to each fraction collected from the column stabilize the product. Upon removal of the solvent, there is obtained 7.9 g, (86%) of ethyl 1-(2-acetoxyethyl)-4-bromopyrrol-2-acetate, an unstable oil exhibiting the following characteristics:

U.V.: 218,307 nm ($\epsilon$6610, 275).

I.R.: (CHCl$_3$).

N.M.R.: (CDCl$_3$); 1.25 (t, 3H, J=7.3); 2.05 (s, 3H); 3.60 (s, 2H); 3.98–4.34 (m, 6H); 6.07 (d, 1H, J=1.8); 6.66 (d, 1H, J=1.8).

PREPARATION V

Alkyl 1-(2-Hydroxyethyl)4-chloropyrrol-2-acetate.

A. Twenty-six g. of ethyl 1-(2-acetoxyethyl)-4-chloropyrrole-2-acetate (0.095 ml.) is dissolved in 260 ml. of anhydrous methanol and 10 drops of DBN is added. The solution is stirred at room temperature, in a nitrogen atmosphere, for 6 hours. Two and a half l. of an aqueous saturated solution of sodium chloride is added and the product is extracted into ethyl acetate. The organic phase is washed with a saturated sodium chloride solution, dried over sodium sulphate and evaporated in vacuo to give 20.1 g. of methyl 1-(2-hydroxyethyl)-4-chloropyrrol-2-acetate (VIII, Y is Cl), an oil having the following physical constants:

U.V.: 207.5, 216 nm ($\epsilon$6030, 5090).
I.R.: 3590, 3500, 1732 cm$^{-1}$ (CHCl$_3$).
N.M.R.: (CDCl$_3$); 2.74 (s, W$_H$=4, exchanged with D$_2$O); 3.58 (s, 2H); 3.61–3.92 (m, 4H); 3.67 (s, 3H); 6.27 (d, 1H, J=2.0); 6.58 (d, 1H, J=2.0).
M.S.: 217 (M+).
Calcd. for C$_9$H$_{12}$ClNO$_3$: C, 49.66; H, 5.55; N, 6.43. Found: C, 49.63; H, 5.46; N, 6.53.

B. Methyl 1-(2-hydroxyethyl)-4-bromopyrrol-2-acetate

A solution of 8.0 g, 25.0 mmole) of the pyrrole from Preparation IV, Part B, in 100 ml anhydrous methanol containing 1,5-diazabicyclo[4.3.0]nonene-5 (5 drops) is left at room temperature in an argon atmosphere for 18 hours. The solvent is removed in vacuo, the residue is dissolved in ethyl acetate, the solution washed with saturated salt solution, dried over sodium sulfate and evaporated in vacuo to give methyl 1-(2-hydroxyethyl)-4-bromopyrrole-2-acetate, (VIII, Y is Br) an oil having the following physical constants:

U.V.: 218 nm ($\epsilon$5620).
I.R.: (CHCl$_3$); 3600, 3520, 3440, 1740 cm$^{-1}$.
N.M.R.: (CDCl$_3$); 2.78 (s, 1H, exchanged with D$_2$O); 3.55–4.02 (m, 4H); 3.65 (s, 2H); 3.72 (s, 3H); 6.06 (d, 1H, J=1.5); 6.71 (d, 1H, J=1.5).

PREPARATION VI

Methyl 1-(2-iodoethyl)-4-chloropyrrol-2-acetate.

A. Twenty g. (0.092 mol.) of methyl 1-(2-hydroxyethyl)-4-chloropyrrol-2-acetate is dissolved in 500 ml. of anhydrous dichloromethane and cooled to 0°. Methanesulfonyl chloride (8.53 ml., 0.11 mol.) is added all at once and after stirring for 5 minutes, 15.3 ml. of triethylamine (0.11 mol.) is added in a dropwise manner. The reaction mixture is then stirred at room temperature for 1 hour. The solvent is removed in vacuo and the residue is dissolved in dichloromethane, washed with aqueous saturated sodium chloride until neutral, dried over sodium sulphate and evaporated in vacuo to give 29.8 g. of a crude methyl 1-(2-methanesulfonyloxyethyl)-4-chloropyrrol-2-acetate (IX, Y is Cl).

Twenty-nine g. of the resulting mesylate (0.098 mol.) is dissolved in 700 ml. of acetonitrile and 73 g. of anhydrous sodium iodide (0.49 mol.) is added. The mixture is heated at reflux temperature for 2 hours. The precipitate which forms is removed by filtration and washed with dichloromethane. The filtrate is evaporated to dryness in vacuo and the residue is dissolved in ethyl acetate, washed to neutrality with water, dried over sodium sulphate and evaporated in vacuo. The crude product (32.9 g.) is purified by column chromatography on silica gel using hexane-ethyl acetate (95:5) as the developing solvent to give 26.1 g. methyl 1-(2-iodoethyl)-4-chloropyrrol-2-acetate (X, Y is Cl), an oil having the following physical constants:

U.V.: 221.5 nm ($\epsilon$7250).
I.R.: 1736 cm$^{-1}$ (CHCl$_3$).
N.M.R.: (CDCl$_3$), 3.29 (t, 2H, J=7.5); 3.57 (s, 2H); 3.70 (s, 3H); 4.15 (t, 2H, J=7.5); 5.98 (d, 2H, J=1.8); 6.67 (d, 2H, J=1.8).
M.S.: 327,329 (M+).

PREPARATION VII

Methyl 1-(2-methanesulfonyloxyethyl)-4-bromopyrrol-2-acetate

To a stirred solution of 5.8 g, (22.0 mmole) of the pyrrole of Preparation VI, Part B, in anhydrous dichloromethane (60 ml), cooled to 0° C. and maintained in an atmosphere of argon, is added 2.0 ml (26.5 mmole) of methanesulfonyl chloride followed by 3.7 ml (26.4 mmole) of triethylamine, added dropwise. The reaction is left to come to room temperature and after a further 30 minutes the solvent is removed in vacuo. The residue is dissolved in dichloromethane, washed well with saturated salt solution, dried and evaporated. The residue is subjected to column chromatography on silica gel (after the addition of a few drops of triethylamine) using hexane-ethyl acetate (7:3) to give a solution which, when evaporated, gives 6.0 g (80%) of methyl 1-(2-methanesulfonyloxyethyl)-4-bromopyrrol-2-acetate (IX, Y is Br), an oil having the following physical constants:

U.V.: 223 nm. ($\epsilon$5370).
I.R.: (CHCl$_3$); 1744, 1356, 1166, cm$^{-1}$.
N.M.R.: (CDCl$_3$); 2.85 (s, 3H); 3.60 (s, 2H); 3.69 (s, 3H); 4.02–4.48 (m, 4H); 6.06 (d, 1H, J=1.6); 6.68 (d, H, J=1.6).

EXAMPLE 1

Methyl 6-chloro-1,2-dihydro-3H-pyrrolo[1,2-a]pyrrole-1-carboxylate

A. In an atmosphere of argon, 2.52 g. of 50% sodium hydride in mineral oil (0.053 mol.) is washed free of the carrier with dry hexane (2×20 ml.). Thereafter 150 ml. of anhydrous dimethylformamide is added and the mixture is cooled to 0°. To this mixture is added, with stirring, 16.4 g. of methyl 1-(2-iodoethyl)-4-chloropyrrol-2-acetate (0.05 mol.) dissolved in 50 ml. dimethylformamide. The reaction mixture is left at room temperature for 2 hours, when saturated aqueous sodium chloride solution is added and the product extracted into benzene (3×200 ml.). The organic extract is washed with water (2×100 ml.), dried over sodium sulphate and evaporated in vacuo. The crude product (8.52 g.) is purified by column chromatography on silica gel (245 g.) using hexane-ethyl acetate (90:10) as the eluting solvent, to yield methyl 6-chloro-1,2-dihydro-3H-pyrrolo[1,2-a]pyrrole-1-carboxylate, an oil having the following physical constants:

U.V.: 224, 279, 286 nm ($\epsilon$6760, 7420, 6920).
I.R.: 1726 cm$^{-1}$ (CHCl$_3$).
N.M.R.: (CDCl$_3$); 2.37–2.75 (m, 2H); 3.62 (s, 3H); 3.53–4.07 (m, 3H); 5.85 (m, 1H); 6.45 (m, 1H).
M.S.: 201,199 (M+).

EXAMPLE 2

Methyl 6-bromo-1,2-dihydro-3H-pyrrolo[1,2-a]pyrrole-1-carboxylate

Sodium hydride in mineral oil (50%, 0.65 g, 13.6 mmole) is washed free of the carrier with hexane, covered with anhydrous dimethylformamide (20 ml) and then cooled to 0°, in a nitrogen atmosphere, with stirring. The methanesulfonate (4.4 g, 12.9 mmole), prepared in accordance with Preparation VII, in 10 ml of dry dimethylformamide is added in a dropwise manner. The reaction mixture is left at 0° for 3 hours, at which time saturated salt solution (30 ml) is added. The product is extracted into benzene, the extract is washed with water, dried and evaporated. The residue is purified by TLC on silica gel using hexane-ethyl acetate (4:1) as the developing solvent. This yields 1.56 g (49%) of an oil which is crude methyl 6-bromo-1,2-dihydro-3H-pyrrolo[1,2-a]pyrrole-1-carboxylate.

EXAMPLE 3

Methyl 5-benzoyl-6-chloro-1,2-dihydro-3H-pyrrolo[1,2-a]pyrrole-1-carboxylate

A solution of 1.10 g. of methyl 6-chloro-1,2-dihydro-3H-pyrrolo[1,2-a]pyrrole-1-carboxylate (5.5 mmol.) in dry xylene (25 ml.) containing 2.32 g of benzoyl chloride (16.5 mmol.) is heated at reflux temperature for 50 hours. The solvent is removed in vacuo, the residue is dissolved in dichloromethane (50 ml.), the solution is washed sequentially with saturated sodium chloride solution, 10% sodium bicarbonate solution, and saturated sodium chloride solution again. The organic phase is dried over sodium sulfate, evaporated in vacuo and the residue is subjected to column chromatography on silica gel (50:1) using hexane-ethyl acetate (9:1) as the eluting solvent. The solvent is removed and the product is crystallized from hexane to give methyl 5-benzoyl-6-chloro-1,2-dihydro-3H-pyrrolo[1,2-a]pyrrole-1-carboxylate, m.p. 106° C.

EXAMPLE 4

Methyl 5-benzoyl-6-bromo-1,2-dihydro-3H-pyrrolo[1,2-a]-pyrrole-1-carboxylate

A solution of 0.98 ml benzoyl chloride (8.4 mmole) in 5 ml of dry xylene is added in a dropwise manner to a boiling solution of the pyrrolo[1,2-a]pyrrole-1-carboxylate prepared according to EXAMPLE 2 (0.685 g, 2.8 mmole) in 20 ml dry xylene maintained in an atmosphere of argon. The solution is heated at reflux for a further 48 hours. The solvent is removed in vacuo, the residue is dissolved in ethyl acetate, and the solution is washed successively with water, 10% sodium bicarbonate solution, and saturated salt solution. The organic phase is dried over sodium sulfate and evaporated in vacuo. The residue (1.33 g) is subjected to column chromatography on silica gel using hexane-ethyl acetate (4:1) to elute the product. The solvent is removed to give 0.79 g of a product which when crystallized from dichloromethane-hexane yields methyl 5-benzoyl-6-bromo-1,2-dihydro-3H-pyrrolo[1,2-a]pyrrole-1-carboxylate, m.p. 93° C.

EXAMPLE 5

A.

5-Benzoyl-6-chloro-1,2-dihydro-3H-pyrrolo[1,2-a]pyrrole-1-carboxylic acid

Methyl 5-benzoyl-6-chloro-1,2-dihydro-3H-pyrrolo[1,2-a]pyrrole-1-carboxylate (1.10 g.) in 30 ml. of methanol containing 2 molar equivalents potassium carbonate in 10 ml. of water is heated at reflux temperature for three hours. The methanol is removed in vacuo and water is added to the residue. The solution is extracted with ethyl acetate, the aqueous phase is cooled to 0° and made acidic with 20% hydrochloric acid. The solid which precipitates is collected by filtration, washed with cold water and dried in vacuo. The residue is crystallized from methanol-water to give 5-benzoyl-6-chloro-1,2-dihydro-3H-pyrrolo[1,2-a]pyrrole-1-carboxylic acid, m.p. 190° C.

B.

5-Benzoyl-6-bromo-1,2-dihydro-3H-pyrrolo[1,2-a]pyrrole-1-carboxylic acid.

By following in principle the procedure of Part A of this Example but substituting methyl 5-benzoyl-6-bromo-1,2-dihydro-3H-pyrrolo[1,2-a]pyrrole-1-carboxylate for methyl 5-benzoyl-6-chloro-1,2-dihydro-3H-pyrrolo[1,2-a]pyrrole-1-carboxylate, one obtains upon crystallizing from ethyl acetate-hexane 5-benzoyl-6-bromo-1,2-dihydro-3H-pyrrolo[1,2-a]-pyrrole-1-carboxylic acid, m.p. 199° C.

EXAMPLE 6

A. Methyl 5-substituted benzoyl-6-chloro-1,2-dihydro-3H-pyrrolo[1,2-a]pyrrole-1-carboxylates By following in principle the procedure of Example 3, Part A but substituting for benzoyl chloride, the following substituted benzoyl chlorides:

m-fluorobenzoyl chloride,
o-fluorobenzoyl chloride,
p-fluorobenzoyl chloride,
m-chlorobenzoyl chloride,
o-chlorobenzoyl chloride,
p-chlorobenzoyl chloride,
m-methylbenzoyl chloride,
o-methylbenzoyl chloride,
p-methylbenzoyl chloride,
p-butylbenzoyl chloride,
m-methoxybenzoyl chloride,
o-methoxybenzoyl chloride,
p-methoxybenzoyl chloride,
p-butoxybenzoyl chloride,
m-methylthiobenzoyl chloride,
o-methylthiobenzoyl chloride,
p-methylthiobenzoyl chloride, and
p-butylthiobenzoyl chloride, one respectively obtains the following compounds of this invention:

methyl 5-m-fluorobenzoyl-6-chloro-1,2-dihydro-3H-pyrrolo[1,2-a]pyrrole-1-carboxylate,
methyl 5-o-fluorobenzoyl-6-chloro-1,2-dihydro-3H-pyrrolo[1,2-a]pyrrole-1-carboxylate,
methyl 5-p-fluorobenzoyl-6-chloro-1,2-dihydro-3H-pyrrolo[1,2-a]pyrrole-1-carboxylate, m.p. 117° C.,
methyl 5-m-chlorobenzoyl-6-chloro-1,2-dihydro-3H-pyrrolo[1,2-a]pyrrole-1-carboxylate,
methyl 5-o-chlorobenzoyl-6-chloro-1,2-dihydro-3H-pyrrolo[1,2-a]pyrrole-1-carboxylate,
methyl 5-p-chlorobenzoyl-6-chloro-1,2-dihydro-3H-pyrrolo[1,2-a]pyrrole-1-carboxylate, m.p. 85° C.,
methyl 5-m-methylbenzoyl-6-chloro-1,2-dihydro-3H-pyrrolo[1,2-a]pyrrole-1-carboxylate,
methyl 5-o-methylbenzoyl-6-chloro-1,2-dihydro-3H-pyrrolo[1,2-a]pyrrole-1-carboxylate, methyl 5-p-methylbenzoyl-6-chloro-1,2-dihydro-3H-pyrrolo[1,2-a]pyrrole-1-carboxylate, m.p. 86° C.,
methyl 5-p-butylbenzoyl-6-chloro-1,2-dihydro-3H-pyrrolo[1,2-a]pyrrole-1-carboxylate,
methyl 5-m-methoxybenzoyl-6-chloro-1,2-dihydro-3H-pyrrolo[1,2-a]pyrrole-1-carboxylate,
methyl 5-o-methoxybenzoyl-6-chloro-1,2-dihydro-3H-pyrrolo[1,2-a]pyrrole-1-carboxylate,
methyl 5-p-methoxybenzoyl-6-chloro-1,2-dihydro-3H-pyrrolo[1,2-a]pyrrole-1-carboxylate, m.p. 111° C.,
methyl 5-p-butoxybenzoyl-6-chloro-1,2-dihydro-3H-pyrrolo[1,2-a]pyrrole-1-carboxylate,
methyl 5-m-methylthiobenzoyl-6-chloro-1,2-dihydro-3H-pyrrolo[1,2-a]pyrrole-1-carboxylate,
methyl 5-o-methylthiobenzoyl-6-chloro-1,2-dihydro-3H-pyrrolo[1,2-a]pyrrole-1-carboxylate,
methyl 5-p-methylthiobenzoyl-6-chloro-1,2-dihydro-3H-pyrrolo[1,2-a]pyrrole-1-carboxylate, m.p. 100° C.,
methyl 5-p-butylthiobenzoyl-6-chloro-1,2-dihydro-3H-pyrrolo[1,2-a]pyrrole-1-carboxylate,

B. Methyl 5-substituted benzoyl-6-bromo-1,2-dihydro-3H-pyrrolo[1,2-a]pyrrolo-1-carboxylate By following in principle the procedure of Part A of this Example, but substituting methyl 6-bromo-1,2-dihydro-3H-pyrrolo[1,2-a]pyrrole-1-carboxylate of Example 2, for methyl 6-chloro-1,2-dihydro-3H-pyrrolo[1,2-a]pyrrole-1-carboxylate, one obtains the 6-bromo compounds of this invention which correspond to the 6-chloro compounds listed above in Part A such as methyl 5-m-flurobenzoly-6-bromo-1,2-dihydro-3H-pyrrolo[1,2-a]pyrrole-1-carboxylate,
methyl 5-p-fluorobenzoyl-6-bromo-1,2-dihydro-3H-pyrrolo[1,2-a]pyrrole-1-carboxylate, m.p. 131° C. (dichloromethane-hexane) and the like.

EXAMPLE 7

A. 5-Substituted benzoyl-6-chloro-1,2-dihydro-3H-pyrrolo[1,2-a]pyrrole-1-carboxylic acids By following in principle the procedure of Example 5 but substituting the esters prepared in Example 6, Part A, for methyl benzoyl-6-chloro-1,2-dihydro-3H-pyrrolo[1,2-a]pyrrole-1-carboxylate, one obtains 5-m-fluorobenzoyl-6-chloro-1,2-dihydro-3H-pyrrolo[1,2-a]pyrrole-1-carboxylic acid,
5-o-fluorobenzoyl-6-chloro-1,2-dihydro-3H-pyrrolo[1,2-a]pyrrole-1-carboxylic acid,
5-p-fluorobenzoyl-6-chloro-1,2-dihydro-3H-pyrrolo[1,2-a]pyrrole-1-carboxylic acid, m.p. 206° C.,
5-m-chlorobenzoyl-6-chloro-1,2-dihydro-3H-pyrrolo[1,2-a]pyrrole-1-carboxylic acid,
5-o-chlorobenzoyl-6-chloro-1,2-dihydro-3H-pyrrolo[1,2-a]pyrrole-1-carboxylic acid,
5-p-chlorobenzoyl-6-chloro-1,2-dihydro-3H-pyrrolo[1,2-a]pyrrole-1-carboxylic acid, m.p. 200° C.,
5-m-methylbenzoyl-6-chloro-1,2-dihydro-3H-pyrrolo[1,2-a]pyrrole-1-carboxylic acid,
5-o-methylbenzoyl-6-chloro-1,2-dihydro-3H-pyrrolo[1,2-a]pyrrole-1-carboxylic acid,
5-p-methylbenzoyl-6-chloro-1,2-dihydro-3H-pyrrolo[1,2-a]pyrrole-1-carboxylic acid, m.p. 198° C.,
5-p-butylbenzoyl-6-chloro-1,2-dihydro-3H-pyrrolo[1,2-a]pyrrole-1-carboxylic acid,
5-m-methoxybenzoyl-6-chloro-1,2-dihydro-3H-pyrrolo[1,2-a]pyrrole-1-carboxylic acid,
5-o-methoxybenzoyl-6-chloro-1,2-dihydro-3H-pyrrolo[1,2-a]pyrrole-1-carboxylic acid,
5-p-methoxybenzoyl-6-chloro-1,2-dihydro-3H-pyrrolo[1,2-a]pyrrole-1-carboxylic acid, m.p. 182° C.,
5-p-butoxybenzoyl-6-chloro-1,2-dihydro-3H-pyrrolo[1,2-a]pyrrole-1-carboxylic acid,
5-m-methylthiobenzoyl-6-chloro-1,2-dihydro-3H-pyrrolo[1,2-a]pyrrole-1-carboxylic acid,
5-o-methylthiobenzoyl-6-chloro-1,2-dihydro-3H-pyrrolo[1,2-a]pyrrole-1-carboxylic acid,
5-p-methylthiobenzoyl-6-chloro-1,2-dihydro-3H-pyrrolo[1,2-a]pyrrole-1-carboxylic acid, m.p. 197° C.,
5-p-butylthiobenzoyl-6-chloro-1,2-dihydro-3H-pyrrolo[1,2-a]pyrrole-1-carboxylic acid,

B. 5-Substituted benzoyl-6-bromo-1,2-dihydro-3H-pyrrolo[1,2-a]pyrrole-1-carbozylic acid In a similar manner, by following in principle Part A of this example, the compounds which are prepared according to Example 6, Part B are converted to the corresponding acids such as 5-m-fluorobenzoyl-6-bromo-1,2-dihydro-3H-pyrrole[1,2-a]pyrrole-1-carboxylic acid,
5-p-fluorobenzoyl-6-bromo-1,2-dihydro-3H-pyrrole[1,2-a]pyrrole-1-carboxylic acid, m.p. 217° C. (ethyl acetate), and the like.

EXAMPLE 8

A. Methyl 5-(4-methylsulfinylbenzoyl)-6-chloro-1,2-dihydro-3H-pyrrolo[1,2-a]pyrrole-1-carboxylate Two hundred mg of sodium periodate is added to a solution of methyl 5-(4-methylthiobenzoyl)-6-chloro-1,2-dihydro-3H-pyrrolo[1,2-a]pyrrole-6-carboxylate (0.150 g) in methanol (5 ml) and tetrahydrofuran (2 ml), cooled to 0°. After 18 hours at room temperature, the mixture is poured into water, the precipitated solid is collected by filtration, washed with water and dried. Crystallization of this material from dichloromethanemethanol gives methyl 4-(4-methylsulfinylbenzoyl)-6-chloro-1,2-dihydro-3H-pyrrolo[1,2-a]pyrrole-6-carboxylate.

B. Methyl 5-(4-methylsulfinylbenzoyl)-6-bromo-1,2-dihydro-3H-pyrrolo[1,2-a]pyrrole-1-carboxylate Similarly, by following the procedure of Part A of this example, but substituting methyl 5-(4-methylthiobenzoyl)-6-bromo-1,2-dihydro-3H-pyrrolo[1,2-a]pyrrole-6-carboxylate for methyl 5-(4-methylthiobenzoyl)-6-chloro-1,2-dihydro-3H-pyrrolo[1,2-a]pyrrole-6-carboxylate one obtains methyl 5-(4-methylsulfinylbenzoyl)-6-bromo-1,2-dihydro-3H-pyrrolo[1,2-a]pyrrole-6-carboxylate.

EXAMPLE 9

A. 5-(4-Methylsulfinylbenzoyl)-6-chloro-1,2-dihydro-3H-pyrrolo[1,2-a]pyrrole-1-carboxylic acid By following in principle the procedure of Example 5 but substituting methyl 5-(4-methylsulfinylbenzoyl)-6-chloro-1,2-dihydro-3H-pyrrolo[1,2-a]pyrrole-1-carboxylate for methyl benzoyl-6-chloro-1,2-dihydro-3H- pyrrolo[1,2-a]pyrrole-1-carboxylate one obtains 5-(4-methylsulfinylbenzoyl)-6-chloro-1,2-dihydro-3H-pyrrolo[1,2-a]pyrrole-1-carboxylic acid.

B.
5-(4-methylsulfinylbenzoyl)-6-bromo-1,2-dihydro-3H-pyrrolo[1,2-a]pyrrole-1-carboxylic acid By following in principle the procedure of Example 5 but substituting methyl 5-(4-methylsulfinylbenzoyl)-6-bromo-1,2-dihydro-3H-pyrrolo[1,2-a]pyrrole-1-carboxylate for methyl benzoyl-6-chloro-1,2-dihydro-3H-pyrrolo[1,2-a]pyrrole-1-carboxylate one obtains 5-(4-methylsulfinylbenzoyl)-6-bromo-1,2-dihydro-3H-pyrrolo[1,2-a]pyrrole-1-carboxylic acid.

EXAMPLE 10

Methyl 5-p-methylsulfonylbenzoyl-6-chloro and 6-bromo-1,2-dihydro-3H-pyrrolo[1,2-a]pyrrole-1-carboxylate A. To a stirred solution of 1.13 g. of methyl 5-(4-methylthio)benzoyl-6-chloro-1,2-dihydro-3H-pyrrolo[1,2-a]pyrrole-1-carboxylate (3.23 mmol.) in 100 ml. of dry dichloromethane, maintained at 0°, is added a solution of 1.9 g. of m-chloroperbenzoic acid (9.69 mmol.) in 20 ml. of dry dichloromethane. When the addition is complete, stirring at this temperature is continued for 40 minutes, at which time 30 ml. of a saturated solution of sodium bicarbonate is added. The organic phase is separated from the aqueous phase, washed to neutrality with saturated aqueous sodium chloride solution, dried over sodium sulfate and evaporated in vacuo. The crude product (2.2 g.) is subjected to column chromatography on silica gel (110 g.). The column is developed first with hexane-ethyl acetate (7:3) and then 1:1 ethyl acetate-hexane. The product (0.84 g.), on crystallization from acetone-hexane, gives 0.74 g. of methyl 5-p-methylsulfonylbenzoyl-6-chloro-1,2-dihydro-3H-pyrrolo[1,2-a]pyrrole-1-carboxylate, m.p. 155° C. B. Similarly, by following in principle the procedure of Part A of this Example but substituting methyl 5-p-methylthiobenzoyl-6-bromo-1,2-dihydro-3H-pyrrolo[1,2-a]pyrrole-1-carboxylate for methyl 5-p-methylthiobenzoyl-6-chloro-1,2-dihydro-2H-pyrrolo[1,2-a]pyrrole-1-carboxylate, one obtains methyl-p-methylsulfonylbenzoyl-6-bromo-1,2-dihydro-3H-pyrrolo[1,2-a]pyrrole-1-carboxylate.

EXAMPLE 11

5-(4-methylsulfonylbenzoyl)-6-chloro and 6-bromo-1,2-dihydro-3H-pyrrolo[1,2-a]pyrrole-1-carboxylic acid A. By following in principle the procedure of Example 5, Part A but substituting the esters prepared in Example 10, Parts A and B for methyl 5-benzoyl-6-chloro-1,2-dihydro-3H-pyrrolo[1,2-a]pyrrole-1-carboxylate, one obtains 5-p-methylsulfonylbenzoyl-6-chloro-1,2-dihydro-3H-pyrrolo[1,2-a]pyrrole-1-carboxylic acid and
5-p-methylsulfonylbenzoyl-6-bromo-1,2-dihydro-3H-pyrrolo[1,2-a]pyrrole-1-carboxylic acid.

EXAMPLE 12

A. Methyl 5-(3-thenoyl)-6-chloro-1,2-dihydro-3H-pyrrolo[1,2-a]pyrrole-1-carboxylates A solution of 232.5 mg. of N,N-dimethylthiophene-3-carboxamide and 0.15 ml of phosphorous oxychloride in 2 ml. of 1,2-dichloroethane is refluxed for 30 minutes. To this solution is added a solution of 181 mg. of methyl 6-chloro-1,2-dihydro-3H-pyrrolo[1,2-a]pyrrole-1-carboxylate in 2 ml of 1,2-dichloroethane. The reaction mixture is reluxed under an argon atmosphere for 8 hours, treated with 450 mg. of sodium acetate and refluxed for a further 5 hours. The resultant mixture is then evaporated to dryness and the residue is chromatographed on 12 g. of silica gel, eluting with hexane:ethyl acetate (3:1), thus obtaining methyl 5-(3-thenoyl)-6-chloro-1,2-dihydro-3H-pyrrolo[1,2-a]pyrrole-1-carboxylate (the methyl ester of Formula (A3) where X=S, Y=Cl)

B. Methyl 5-(3-thenoyl)-6-bromo-1,2-dihydro-3H-pyrrolo[1,2-a]pyrrole-1-carboxylates Similarly, by following in principle the procedure of Part A of this Example, but substituting methyl 6-bromo-1,2-dihydro-3H-pyrrolo[1,2-a]pyrrole-1-carboxylates of Example 2 for 6-chloro-1,2-dihydro-3H-pyrrolo[1,2-a]pyrrole-1-carboxylate, one obtains methyl 5-(3-thenoyl)-6-bromo-1,2-dihydro-3H-pyrrolo[1,2-a]pyrrole-1-carboxylate.

EXAMPLE 13

5-(3-thenoyl)-6-chloro- and 6-bromo-1,2-dihydro-3H-pyrrolo[1,2-a]pyrrole-1-carboxylic acids By hydrolyzing the carboxylates of Example 12 in accordance with the procedure of Example 5, Part A, one obtains 5-(3-thenoyl)-6-chloro-1,2-dihydro-3H-pyrrolo-[1,2-a]pyrrole-1-carboxylic acid and
5-(3-thenoyl)-6-bromo-1,2-dihydro-3H-pyrrolo[1,2-a]pyrrole-1-carboxylic acid.

EXAMPLE 14

Methyl 5-(3-furoyl)-6-chloro- or 6-bromo-1,2-dihydro-3H-pyrrolo[1,2-a]pyrrole-1-carboxylate By following in principle the procedure of Example 12, Parts A and B but substituting N,N-dimethylfuran-3-carboxamide for N,N-dimethylthiophene-3-carboxamide, one obtains methyl 5-(3-furoyl)-6-chloro-1,2-dihydro-3H-pyrrolo[1,2-a]pyrrole-1-carboxylate and
methyl 5-(3-furoyl)-6-bromo-1,2-dihydro-3H-pyrrolo[1,2-a]pyrrole-1-carboxylate.

EXAMPLE 15

5-(3-furoyl)-6-chloro- or bromo-1,2-dihydro-3H-pyrrolo[1,2-a]pyrrole-1-carboxylic acids By hydrolyzing the carboxylates of Example 14 in accordance with the procedure of Example 5, one obtains respectively 5-(3-furoyl)-6-chloro-1,2-dihydro-3H-pyrrolo[1,2-a]pyrrole-1-carboxylic acid and
5-(3-furoyl)-6-bromo-1,2-dihydro-3H-pyrrolo[1,2-a]pyrrole-1-carboxylic acid.

EXAMPLE 16

Methyl 5-(2-thenoyl)-6-chloro- or 6-bromo-1,2-dihydro-3H-pyrrolo[1,2-l]pyrrole-1-carboxylate By following in principle the procedure of Example 11, Parts A and B but substituting N,N-dimethylthiophene-2-carboxamide for N,N-dimethylthiophene-3-carboxamide, one obtains methyl 5-(2-thenoyl)-6-chloro-1,2-dihydro-3H-pyrrolo[1,2-a]pyrrole-1-carboxylate and
methyl 5-(2-thenoyl)-6-bromo-1,2-dihydro-3H-pyrrolo[1,2-a]pyrrole-1-carboxylate.

EXAMPLE 17

5-(2-Thenoyl)-6-chloro- or 6-bromo-1,2-dihydro-3H-pyrrolo[1,2-a]pyrrole-1-carboxylic acids By hydrolyzing the carboxylates of Example 16, in accordance with the procedure of Example 4, one obtains respectively the following compounds:

5-(2-thenoyl)-6-chloro-1,2-dihydro-3H-pyrrolo[1,2-a]pyrrole-1-carboxylic acid and
5-(2-thenoyl)-6-bromo-1,2-dihydro-3H-pyrrolo[1,2-a]pyrrole-1-carboxylic acid.

EXAMPLE 18

Methyl 5-(substituted 2-thenoyl)-6-chloro- or 6-bromo-1,2-dihydro-3H-pyrrolo[1,2-a]pyrrole-1-carboxylates A. By following in principle the procedure of Example 12, Part A but substituting N,N-dimethyl-3-methylthiophene-2-carboxamide,
N,N-dimethyl-4-methylthiophene-2carboxamide,
N,N-dimethyl-5-methylthiophene-2-carboxamide,
N,N-dimethyl-4-chlorothiophene-2-carboxamide,
N,N-dimethyl-5-chlorothiophene-2-carboxamide,
N,N-dimethyl-3-bromothiophene-2-carboxamide and
N,N-dimethyl-5-bromothiophene-2-carboxamide for N,N-dimethylthiophene-3-carboxamide, one obtains
methyl 5-(2-3'-methylthenoyl)-6-chloro-1,2-dihydro-3H-pyrrolo[1,2-a]pyrrole-1-carboxylate,
methyl 5-(2-4'-methylthenoyl)-6-chloro-1,2-dihydro-3H-pyrrolo[1,2-a]pyrrole-1-carboxylate,
methyl 5-(2-5'-methylthenoyl)-6-chloro-1,2-dihydro-3H-pyrrolo[1,2-a]pyrrole-1-carboxylate,
methyl 5-(2-4'-chlorothenoyl)-6-chloro-1,2-dihydro-3H-pyrrolo[1,2-a]pyrrole-1-carboxylate,
methyl 5-(2-5'-chlorothenoyl)-6-chloro-1,2-dihydro-3H-pyrrolo[1,2-a]pyrrole-1-carboxylate,
methyl 5-(2-3'-bromothenoyl)-6-chloro-1,2-dihydro-3H-pyrrolo[1,2-a]pyrrole-1-carboxylate and
methyl 5-(2-5'-bromothenoyl)-6-chloro-1,2-dihydro-3H-pyrrolo[1,2-a]pyrrole-1-carboxylate.

B. In like manner, by following the procedure of Part A of this example but substituting methyl 6-bromo-1,2-dihydro-3H-pyrrolo[1,2-a]pyrrole-1-carboxylate for methyl 6-chloro-1,2-dihydro-3H-pyrrolo[1,2-a]pyrrole-1-carboxylate, one obtains the 6-bromo-substituted compounds corresponding to the 6-chloro compounds of Part A of this example.

EXAMPLE 19

5-(substituted 2-Thenoyl)-6-chloro- or 6-bromo-1,2-dihydro-3H-pyrrolo[1,2-a]pyrrole-1-carboxylic acids By hydrolyzing the carboxylates of Example 18, Parts A and B, in accordance with the procedure of Example 5, one obtains respectively the following compounds:

5-(2-3'-methylthenoyl)-6-chloro-1,2-dihydro-3H-pyrrolo[1,2-a]pyrrole-1-carboxylic acid,
5-(2-4'-methylthenoyl)-6-chloro-1,2-dihydro-3H-pyrrolo[1,2-a]pyrrole-1-carboxylic acid,
5-(2-5'-methylthenoyl)-6-chloro-1,2-dihydro-3H-pyrrolo[1,2-a]pyrrole-1-carboxylic acid,
5-(2-4'-chlorothenoyl)-6-chloro-1,2-dihydro-3H-pyrrolo[1,2-a]pyrrole-1-carboxylic acid,
5-(2-5'-chlorothenoyl)-6-chloro-1,2-dihydro-3H-pyrrolo[1,2-a]pyrrole-1-carboxylic acid,
5-(2-3'-bromothenoyl)-6-chloro-1,2-dihydro-3H-pyrrolo[1,2-a]pyrrole-1-carboxylic acid, and 5-(2-5'-bromothenoyl)-6-chloro-1,2-dihydro-3H-pyrrolo[1,2-a]pyrrole-1-carboxylic acid; and
5-(2-3'-methylthenoyl)-6-bromo-1,2-dihydro-3H-pyrrolo[1,2-a]pyrrole-1-carboxylic acid,
5-(2-4'-methylthenoyl)-6-bromo-1,2-dihydro-3H-pyrrolo[1,2-a]pyrrole-1-carboxylic acid,
5-(2-5'-methylthenoyl)-6-bromo-1,2-dihydro-3H-pyrrolo[1,2-a]pyrrole-1-carboxylic acid,
5-(2-4'-chlorothenoyl)-6-bromo-1,2-dihydro-3H-pyrrolo[1,2-a]pyrrole-1-carboxylic acid,
5-(2-5'-chlorothenoyl)-6-bromo-1,2-dihydro-3H-pyrrolo[1,2-a]pyrrole-1-carboxylic acid,
5-(2-3'-bromothenoyl)-6-bromo-1,2-dihydro-3H-pyrrolo[1,2-a]pyrrole-1-carboxylic acid, and
5-(2-5'-bromothenoyl)-6-bromo-1,2-dihydro-3H-pyrrolo[1,2-a]pyrrole-1-carboxylic acid;

EXAMPLE 20

Methyl 5-(2-furoyl)-6-chloro- or 6-bromo-1,2-dihydro-3H-pyrrolo[1,2-l]pyrrole-1-carboxylate By following in principle the procedure of Example 12, Parts A and B but substituting N,N-dimethylfuran-2-carboxamide for N,N-dimethylthiophene-3-carboxamide, one obtains methyl 5-(2-furoyl)-6-chloro-1,2-dihydro-3H-pyrrolo[1,2-a]pyrrole-1-carboxylate and
methyl 5-(2-furoyl)-6-bromo-1,2-dihydro-3H-pyrrolo[1,2-a]pyrrole-1-carboxylate.

EXAMPLE 21

5-(2-furoyl)-6-chloro- or bromo-1,2-dihydro-3H-pyrrolo[1,2-a]pyrrole-1-carboxylic acids By hydrolyzing the carboxylates of Example 20, in accordance with the procedure of Example 5, one obtains respectively the following compounds:

5-(2-furoyl)-6-chloro-1,2-dihydro-3H-pyrrolo[1,2-a]pyrrole-1-carboxylic acid and
5-(2-furoyl)-6-bromo-1,2-dihydro-3H-pyrrolo[1,2-a]pyrrole-1-carboxylic acid.

EXAMPLE 22

Methyl 5-(2-substituted 2-furoyl)-6-chloro- or 6-bromo-1,2-dihydro-3H-pyrrolo[1,2-l]pyrrole-1-carboxylates A. By following in principle the procedure of Example 12, Part A but substituting N,N-dimethyl-3-methylfuran-2-carboxamide,
N,N-dimethyl-4-methylfuran-2-carboxamide,
N,N-dimethyl-4-chlorofuran-2-carboxamide,
N,N-dimethyl-5-chlorofuran-2-carboxamide,
N,N-dimethyl-4-bromofuran-2-carboxamide, and
N,N-dimethyl-5-bromofuran-2-carboxamide, for N,N-dimethylthiophene-3-carboxamide, one obtains
methyl 5-(2-3'-methylfuroyl)-6-chloro-1,2-dihydro-3H-pyrrolo[1,2-a]pyrrole-1-carboxylate,
methyl 5-(2-4'-methylfuroyl)-6-chloro-1,2-dihydro-3H-pyrrolo[1,2-a]pyrrole-1-carboxylate,
methyl 5-(2-4'-chlorofuroyl)-6-chloro-1,2-dihydro-3H-pyrrolo[1,2-a]pyrrole-1-carboxylate,
methyl 5-(2-5'-chlorofuroyl)-6-chloro-1,2-dihydro-3H-pyrrolo[1,2-a]pyrrole-1-carboxylate,
methyl 5-(2-4'-bromofuroyl)-6-chloro-1,2-dihydro-3H-pyrrolo[1,2-a]pyrrole-1-carboxylate, and
methyl 5-(2-5'-bromofuryl)-6-chloro-1,2-dihydro-3H-pyrrolo[1,2-a]pyrrole-1-carboxylate.

B. In like manner, by following the procedure of Part A of this example but substituting methyl 6-bromo-1,2-dihydro-3H-pyrrolo[1,2-a]pyrrole-1-carboxylate for methyl 6-chloro-1,2-dihydro-3H-pyrrolo[1,2-a]pyrrole-1-carboxylate one obtains the 6-bromo-substituted compounds corresponding to the 6-chloro compounds of Part A of this example.

EXAMPLE 23

5-(substituted 2-thenoyl)-6-chloro- or 6-bromo-1,2-dihydro-3H-pyrrolo[1,2-a]pyrrole-1-carboxylic acids By hydrolyzing the carboxylates of Example 21 in accordance with the procedure of Example 5, one obtains respectively the following compounds:

5-(2-3'-methylfuroyl)-6-chloro-1,2-dihydro-3H-pyrrolo[1,2-a]pyrrole-1-carboxylic acid,
5-(2-4'-methylfuroyl)-6-chloro-1,2-dihydro-3H-pyrrolo[1,2-a]pyrrole-1-carboxylic acid,
5-(2-4'-chlorofuroyl)-6-chloro-1,2-dihydro-3H-pyrrolo[1,2-a]pyrrole-1-carboxylic acid,
5-(2-5'-chlorofuroyl)-6-chloro-1,2-dihydro-3H-pyrrolo[1,2-a]pyrrole-1-carboxylic acid,
5-(2-4'-bromofuroyl)-6-chloro-1,2-dihydro-3H-pyrrolo[1,2-a]pyrrole-1-carboxylic acid, and
5-(2-5'-bromofuroyl)-6-chloro-1,2-dihydro-3H-pyrrolo[1,2-a]pyrrole-1-carboxylic acid and the corresponding 6-bromo analogues.

EXAMPLE 24

Methyl 5-(2-pyrroloyl)-6-chloro- or 6-bromo-1,2-dihydro-3H-pyrrolo[1,2a]pyrrole-1-carboxylate A. By following in principle the procedure of Example 12, Part A but substituting N,N-dimethylpyrrole-2-carboxamide for N,N-dimethylthiophene-3-carboxamide, one obtains methyl 5-(2-pyrroloyl)-6-chloro-1,2-dihydro-3H-pyrrolo[1,2-a]pyrrole-1-carboxylate (the methyl ester of $A_3$ where Q is H and Y is Cl).

B. In like manner, by following the procedure of Part A of this example but substituting methyl 6-bromo-1,2-dihydro-3H-pyrrolo[1,2-a]pyrrole-1-carboxylate for methyl 6-chloro-1,2-dihydro-3H-pyrrolo[1,2-a]pyrrole-1-carboxylate one obtains methyl 5-(2-pyrroloyl)-6-bromo-1,2-dihydro-3H-pyrrolo[1,2-a]pyrrole-1-carboxylate,

EXAMPLE 25

5-(2-Pyrroloyl)-6-chloro- or 6-bromo-1,2-dihydro-3H-pyrrolo[1,2-a]pyrrole-1-carboxylic acids By hydrolyzing the carboxylates of Example 24, in accordance with the procedure of Example 5, one obtains respectively the following compounds:

5-(2-pyrroloyl)-6-chloro-1,2-dihydro-3H-pyrrolo[1,2-a]pyrrole-1-carboxylic acid, and
5-(2-pyrroloyl)-6-bromo-1,2-dihydro-3H-pyrrolo[1,2-a]pyrrole-1-carboxylic acid.

EXAMPLE 26

Methyl 5-(2-N-alkylpyrroloyl)-6-chloro- or 6-bromo-1,2-dihydro-3H-pyrrolo[1,2-a]pyrrole-1-carboxylate A. By following in principle the procedure of Example 12, Part A but substituting N,N-dimethyl-1-methylpyrrole-2-carboxamide,
N,N-dimethyl-1-ethylpyrrole-2-carboxamide,
N,N-dimethyl-1-propylpyrrole-2-carboxamide, and
N,N-dimethyl-1-butylpyrrole-2-carboxamide for N,N-dimethylthiophene-3-carboxamide, one obtains methyl 5-(2-N-methypyrroloyl)-6-chloro-1,2-dihydro-3H-pyrrolo[1,2-a]pyrrole-1-carboxylate;
methyl 5-(2-N-ethylpyrroloyl)-6-chloro-1,2-dihydro-3H-pyrrolo[1,2-a]pyrrole-1-carboxylate;
methyl 5-(2-N-propylpyrroloyl)-6-chloro-1,2-dihydro-3H-pyrrolo[1,2-a]pyrrole-1-carboxylate; and
methyl 5-(2-N-butylpyrroloyl)-6-chloro-1,2-dihydro-3H-pyrrolo[1,2-a]pyrrole-1-carboxylate.

B. In like manner, by following the procedure of Part A of this example but substituting methyl 6-bromo1,2-dihydro-3H-pyrrolo[1,2-a]pyrrole-1-carboxylate for 6-chloro-1,2-dihydro-3H-pyrrolo[1,2-a]pyrrole-1-carboxylate one obtains the 6-bromo analogues corresponding to the 6-chloro compounds of Part A of this Example.

EXAMPLE 27

5-(2-N-alkylpyrroloyl)-6-chloro- or 6-bromo-1,2-dihydro-3H-pyrrolo[1,2-a]pyrrole-1-carboxylic acids By hydrolyzing the carboxylates of Example 26 in accordance with the procedure of Example 5, one obtains respectively the following compounds:

5-(2-N-methylpyrroloyl)-6-chloro-1,2-dihydro-3H-pyrrolo[1,2-a]pyrrole-1-carboxylic acid;
5-(2-N-ethylpyrroloyl)-6-chloro-1,2-dihydro-3H-pyrrolo[1,2-a]pyrrole-1-carboxylic acid;
5-(2-N-propylpyrroloyl)-6-chloro-1,2-dihydro-3H-pyrrolo[1,2-a]pyrrole-1-carboxylic acid; and
5-(2-N-butylpyrroloyl)-6-chloro-1,2-dihydro-3H-pyrrolo[1,2-a]pyrrole-1-carboxylic acid and the 6-bromo analogues corresponding to the 6-chloro compounds of this example.

EXAMPLE 28

A solution of 200 mg of 5-benzoyl-6-chloro-1,2-dihydro-3H-pyrrolo[1,2-a]pyrrole-1-carboxylic acid in 5 ml of dichloromethane is treated with an excess of ethereal diazomethane, and the reaction mixture is maintained at room temperature for 30 minutes. The solvents and excess reagent are eliminated under reduced pressure and the residue crystallized from ethyl acetate-methanol, to yield methyl 5-benzoyl-b 1,2-dihydro-3H-pyrrolo[1,2-a]pyrrole-1-carboxylate.

Likewise but using diazoethane, diazopropane and diazobutane in place of diazomethane there are respectively obtained ethyl 5-benzoyl-6-chloro-1,2-dihydro-3H-pyrrolo[1,2-a]pyrrole-1-carboxylate,
propyl 5-benzoyl-6-chloro-1,2-dihydro-3H-pyrrolo[1,2-a]pyrrole-1-carboxylate and
butyl 5-benzoyl-6-chloro-1,2-dihydro-3H-pyrrolo[1,2-a]pyrrole-1-carboxylate.

In a similar manner, the remaining free acids obtained in Examples 5, 7, 9, 11, 13, 15, 17, 19, 21, 23, 25 and 27 are converted into the corresponding methyl, ethyl, propyl and butyl esters.

EXAMPLE 29

A solution of 300 mg of 5-p-chlorobenzoyl-6-chloro-1,2-dihydro-3H-pyrrolo[1,2-a]pyrrole-1-carboxylic acid in 5 ml of isoamyl alcohol is saturated with hydrogen chloride. After 24 hours, the excess alcohol is distilled off in vacuo and the residue purified by chromatography on alumina, to yield isoamyl 5-p-toluoyl-1,2-dihydro-3H-pyrrolo[1,2-a]pyrrole-1-carboxylate.

Likewise other esters, e.g., pentyl, hexyl, octyl, nonyl, dodecyl, and the like are obtained by substituting other alcohols, e.g., pentyl, hexyl, octyl, nonyl, dodecyl alcohol, and the like, for isoamyl alcohol, for example pentyl 5-p-chlorobenzoyl-6-chloro-1,2-dihydro-3H-pyrrolo[1,2-a]pyrrole-1-carboxylate,
hexyl 5-p-chlorobenzoyl-6-chloro-1,2-dihydro-3H-pyrrolo[1,2-a]pyrrole-1-carboxylate,
octyl 5-p-chlorobenzoyl-6-chloro-1,2-dihydro-3H-pyrrolo[1,2-a]pyrrole-1-carboxylate,
nonyl 5-p-chlorobenzoyl-6-chloro-1,2-dihydro-3H-pyrrolo[1,2-a]pyrrole-1-carboxylate,
dodecyl 5-p-chlorobenzoyl-6-chloro-1,2-dihydro-3H-pyrrolo[1,2-a]pyrrole-1-carboxylate, By the same method the free acid compounds obtained in Examples 5, 7, 9, 11, 13, 15, 17, 19, 21, 23, 25 and 27 are esterified with the appropriate alcohol thus obtaining the corresponding esters.

EXAMPLE 30

To a solution of 300 mg of 5-p-chlorobenzoyl-6-chloro-1,2-dihydro-3H-pyrrolo[1,2a]pyrrole-1-carboxylic acid in 5 ml of methanol is added 1 molar equivalent of sodium hydroxide, in the form of a 0.1 N solution. The solvent is taken up in 2 ml of methanol, followed by precipitation with ether, to yield crude sodium 5-p-chlorobenzoyl-6-chloro-1,2-dihydro-3H-pyrrolo[1,2-a]pyrrole-1-carboxylate which can be crystalized from ethyl acetate-hexane.

Likewise other salts, e.g., ammonium and potassium of 5-p-chlorobenzoyl-6-chloro-1,2-dihydro-3H-pyrrolo[1,2-a]pyrrole-1-carboxylic acid are prepared by substituting ammonium hydroxide and potassium hydroxide for sodium hydroxide.

In a similar manner, the 5-substituted-6-chloro or 6-bromo-1,2-dihydro-3H-pyrrolo[1,2-a]pyrrole-1-carboxylic acid compounds obtained in Examples 5, 7, 9, 11, 13, 15, 17, 19, 21, 23, 25 and 27 can be converted into the corresponding sodium, potassium and ammonium salts.

EXAMPLE 31

To a solution of 175 mg of 5-p-chlorobenzoyl-6-chloro-1,2-dihydro-3H-pyrrolo[1,2-a]pyrrole-1-carboxylic acid in 5 ml of methanol is added 1 molar equivalent of potassium hydroxide, in the form of a 0.1 N solution, thus yielding a solution containing potassium 5-p-chlorobenzoyl-6-chloro-1,2-dihydro-3H-pyrrolo[1,2-a]pyrrole-1-carboxylate. A solution of 40 mg of calcium carbonate dissolved in the minimum amount of 1 N hydrochloric acid necessary to effect solution of the calcium carbonate, is buffered with 100 mg of solid ammonium chloride, followed by the further addition of 5 ml of water. The thus obtained buffered calcium solution is then added to the solution of potassium 5-p-chlorobenzoyl-6-chloro-1,2-dihydro-3H-pyrrolo[1,2-a]pyrrole-1-carboxylate and the precipitate which forms is collected by filtration, washed with water and air dried to yield calcium 5-p-chlorobenzoyl-6-chloro-1,2-dihydro-3H-pyrrolo[1,2-a]pyrrole-1-carboxylate.

Likewise, magnesium 5-p-chlorobenzoyl-6-chloro-1,2-dihydro-3H-pyrrolo[1,2-a]pyrrole-1-carboxylate is prepared by substituting magnesium carbonate for calcium carbonate.

Similarly, by substituting other carboxylic acids of Examples 11, 13, 15, 17, 19, 21, 23, 25 and 27 for 5-p-chlorobenzoyl-6-chloro-1,2-dihydro-3H-pyrrolo[1,2-a]pyrrole-1-carboxylic acid there are obtained the corresponding calcium and magnesium salts.

EXAMPLE 32

To a solution of 200 mg of 5-p-chlorobenzoyl-6-chloro-1,2-dihydro-3H-pyrrolo[1,2-a]pyrrole-1-carboxylic acid in 5 ml of methanol is added 1 molar equivalent of potassium hydroxide in the form of a 0.1 N solution. The solvent is stripped and the residue is dissolved in 5 ml of water. The thus obtained aqueous solution of potassium 5-p-chlorobenzoyl-6-chloro-1,2-dihydro-3H-pyrrolo[1,2-a]pyrrole-1-carboxylate is added to a solution of 150 mg of cupric nitrate trihydrate in 5 ml of water. The formed precipitate is collected, washed with water and air dried, thus obtaining copper 5-p-chlorobenzoyl-6-chloro-1,2-dihydro-3H-pyrrolo[1,2-a]pyrrole-1-carboxylate.

In a similar manner the free acid compounds obtained in Examples 11, 13, 15, 17, 19, 21, 23, 25 and 27 can be converted into the corresponding copper salts.

EXAMPLE 33

A solution of 200 mg of 5-p-chlorobenzoyl-6-chloro-1,2-dihydro-3H-pyrrolo[1,2-a]pyrrole-1-carboxylic acid in 15 ml of hot benzene is treated with 60 mg of isopropylamine. The solution is allowed to cool to room temperature and the product filtered off, washed with ether and dried to yield the isopropylamine salt of 5-p-chlorobenzoyl-6-chloro-1,2-dihydro-3H-pyrrolo[1,2-a]pyrrole-1-carboxylic acid.

Likewise other amine salts, e.g., diethylamine, ethanolamine, piperidine, tromethamine, choline and caffeine salts of 5-p-chlorobenzoyl-6-chloro-1,2-dihydro-3H-pyrrolo[1,2-a]pyrrole-1-carboxylic acid are prepared by substituting each of the respective amines for isopropylamine.

In similar manner the free acid compounds obtained in Examples 11, 13, 15, 17, 19, 21, 23, 25 and 27 can be converted into the corresponding isopropylamine, diethylamine, ethanolamine, piperidine, tromethanmine, choline and caffeine salts.

EXAMPLE 34

| Ingredients | Quantity per tablet, mgs. |
|---|---|
| 5-benzoyl-6-chloro-1,2-dihydro-3H-pyrrolo[1,2-a]pyrrole-1-carboxylic acid | 25 |
| cornstarch | 20 |
| lactose, spray-dried | 153 |
| magnesium stearate | 2 |

The above ingredients are thoroughly mixed and pressed into single scored tablets.

Other 1-carboxylic acids or their esters or salts of Examples 2–33 can be substituted for the compound of the above composition.

EXAMPLE 35

| Ingredients | Quantity per capsule, mgs. |
|---|---|
| 5-benzoyl-6-chloro-1,2-dihydro-3H-pyrrolo[1,2-a]pyrrole-1-carboxylic acid | 100 |
| lactose | 148 |
| magnesium stearate | 2 |

The above ingredients are mixed and introduced into a hard-shell gelatin capsule.

Other free acids, their salts or esters of Examples 2–33 can be is substituted for the compound of the above composition.

EXAMPLE 36

| Ingredients | Quantity per capsule, mgs. |
|---|---|
| 5-benzoyl-6-chloro-1,2-dihydro-3H-pyrrolo[1,2-a]pyrrole-1-carboxylic acid | 200 |
| cornstarch | 50 |
| lactose | 145 |
| magensium stearate | 5 |

The above ingredients are mixed intimately and pressed into single scored tablets.

EXAMPLE 37

| Ingredients | Quantity per capsule, mgs. |
|---|---|
| methyl 5-benzoyl-6-chloro-1,2-dihydro-3H-pyrrolo[1,2-a]pyrrole-1-carboxylic acid | 108 |
| lactose | 15 |
| cornstarch | 25 |
| magnesium stearate | 2 |

The above ingredients are mixed and introduced into a hard-shell gelatin capsule.

EXAMPLE 38

| Ingredients | Quantity per capsule, mgs. |
|---|---|
| calcium 5-benzoyl-6-chloro-1,2-dihydro-3H-pyrrolo[1,2-a]pyrrole-1-carboxylic acid | 115 |
| lactose | 93 |
| cornstarch | 40 |
| magensium stearate | 2 |

The above ingredients are mixed and introduced into a hard-shell gelatin capsule.

EXAMPLE 39

| Ingredients | Quantity per capsule, mgs. |
|---|---|
| 5-benzoyl-6-chloro-1,2-dihydro-3H-pyrrolo[1,2-a]pyrrole-1-carboxylic acid | 100 |
| sucrose | 100 |

The above ingredients are thoroughly mixed and processed into single scored tablets.

EXAMPLE 40

| Ingredients | Quantity per capsule, mgs. |
|---|---|
| isoamyl 5-benzoyl-6-chloro-1,2-dihydro-3H-pyrrolo[1,2-a]pyrrole-1-carboxylic acid | 254 |
| cornstarch | 50 |
| lactose | 190 |
| magnesium stearate | 6 |

The above ingredients are mixed intimately and pressed into single scored tablets.

EXAMPLE 41

| Ingredients | Quantity per capsule, mgs. |
|---|---|
| 5-benzoyl-6-chloro-1,2-dihydro-3H-pyrrolo[1,2-a]pyrrole-1-carboxylic acid | 100 |
| lactose | 148 |

-continued

| Ingredients | Quantity per capsule, mgs. |
|---|---|
| dextrose | 2 |

The above ingredients are mixed and introduced into a hard-shell gelatin capsule.

EXAMPLE 42

| Ingredients | Quantity per capsule, mgs. |
|---|---|
| methyl 5-benzoyl-6-chloro-1,2-dihydro-3H-pyrrolo[1,2-a]pyrrole-1-carboxylic acid | 150 |
| lactose | 92 |

The above ingredients are mixed and introduced into a hard-shell gelatin capsule.

EXAMPLE 43

An injectable preparation buffered to a pH of 7 is prepared having the following composition.

| | |
|---|---|
| 5-benzoyl-6-chloro-1,2-dihydro-3H-pyrrolo[1,2-a]pyrrole-1-carboxylic acid | 0.2 g |
| $K_2HPO_4$ buffer (0.4 M solution) | 2 ml. |
| KOH (1N) | q.s. to pH7 |
| water (distilled sterile) | q.s to 20 ml. |

Other 1-carboxylic acids of this invention may be substituted for the compound of the above composition.

EXAMPLE 44

A suppository totaling 2.5 grams is prepared having the following composition:

| | |
|---|---|
| 5-benzoyl-6-chloro-1,2-dihydro-3H-pyrrolo[1,2-a]pyrrole-1-carboxylic acid | 25 mg. |
| Witepsol H-15 (triglycerides of saturated vegetable fatty acids; a product of Riches-Nelson, Inc., New York, N.Y.) | balance |

Other carboxylic acids of this invention may be substituted for the compound of the above composition

EXAMPLE 45

An oral suspension is prepared having the following composition:

| | |
|---|---|
| 5-benzoyl-6-chloro-1,2-dihydro-3H-pyrrolo[1,2-a]pyrrole-1-carboxylic acid | 0.1 g. |
| fumaric acid | 0.5 g. |
| sodium chloride | 2.0 g. |
| methyl paraben | 0.1 g. |
| granulated sugar | 25.5 g. |
| sorbitol (70% solution) | 12.85 g. |
| Veegum K (Vanderbilt Co.) | 1.0 g. |
| flavoring | 0.035 ml. |
| colorings | 0.5 mg. |
| distilled water | q.s. to 100 ml. |

Other carboxylic acids of this invention may be substituted for the compound of the above composition.

EXAMPLE 46-47

Powdered top dressings for veterinary use are prepared having the following compositions:

| | Ex. 46 | Ex. 47 |
|---|---|---|
| 5-benzoyl-6-chloro-1,2-dihydro-3H-pyrrolo[1,2-a]pyrrole-1-carboxylic acid | 0.1 g. | 1.2 g. |
| sucrose | 5.7 g. | 3.7 g. |
| polyvinyl pyrrolidone | 0.3 g. | 0.3 g. |

Other 1-carboxylic acids of this invention may be substituted for the compound of the composition of Example 39 or 40.

EXAMPLE 48

Screening test for anti-inflammatory activity

The oral anti-inflammatory activity is determined utilizing carrageenin induced paw inflammation in the rat in accordance with the method of Winter et al (Pro Soc Exp Biol Med 111:544–547, 1962).

Materials and Methods

Female rats weighing 80–90 grams are used. The test materials are given at hour 0 orally by gavage in 1 ml aqueous vehicle. At hour 1, 0.05 ml of a 1% solution (in 0.9% NaCl) of carrageenin is injected into the right hind paw. This injection causes an inflammation of the paw. The rats are sacrificed at hour 4, at which time both hind paws are removed and weighed separately.

End Point

The % increase in paw size is calculated as follows:

$$\frac{\text{Wt. of Right Paw} - \text{Wt. of Left Paw}}{\text{Wt. of Left Paw}} \times 100$$

The smaller the % increase in paw size, the lesser the degree of inflammation and the greater the anti-inflammatory activity.

Compounds of this invention show anti-inflammatory activity in this test.

EXAMPLE 49

Screening Test for analgetic activity

The oral analgetic activity potential is determined utilizing the mouse analgetic (anti-writhing) assay in accordance with the method of Hendershot and Forsaith (J Pharmacol Exp Ther 125:237–240, 1959)

Materials and Methods

The test material is administered orally by gavage in an aqueous vehicle at time 0 to 18–20 gram male Swiss-Webster mice. Twenty minutes later 0.25 ml of a 0.02% solution of phenylquinone is injected intraperitoneally. This solution induces writhing.

End point

The total number of mice that writhe and the average numbe of writhes per mouse indicates the activity of the compound tested; the fewer writhes per mouse indicates a greater activity.

Compounds of this invention show analgetic activity in this assay.

The subject matter claimed is:

1. A compound selected from the group of those represented by the formula

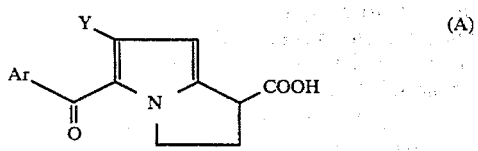

and the pharmaceutically acceptable, non-toxic alkyl esters having from 1 to 12 carbon atoms and salts thereof, wherein
Y is chloro or bromo and
Ar has the formula

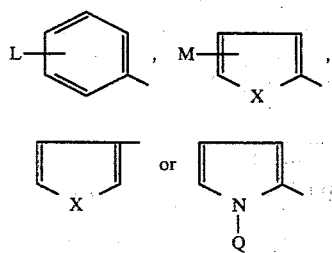

in which
X is sulfur or oxygen;
L is hydrogen, alkyl having 1 to 4 carbon atoms, alkoxy having 1 to 4 carbon atoms, Br, Cl, F, CN, $CF_3$ or $S(O)_nR^3$
wherein $R^3$ is alkyl having 1 to 4 carbon atoms and n is 0, 1 or 2;
M is hydrogen, methyl, Cl or Br; and
Q is hydrogen or alkyl having 1 to 4 carbon atoms.

2. A compound of claim 1 selected from the group in which Ar is

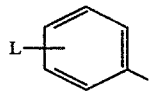

3. A compound of claim 2 wherein Y is chloro and L is methyl, methoxy, methylthio, chloro or fluoro.

4. A compound of claim 3 in which Y is chloro and L is p-methyl, namely 5-p-toluoyl-6-chloro-1,2-dihydro-3H-pyrrolo[1,2-a]pyrrole-1-carboxylic acid and the pharmaceutically acceptable, non-toxic alkyl esters having from one to twelve carbon atoms and salts thereof.

5. The methyl ester of the compound of claim 4, namely methyl 5-toluoyl-6-chloro-1,2-dihydro-3H-pyrrolo[1,2-a]pyrrole-1-carboxylate.

6. A compound of claim 3 in which Y is chloro and L is p-fluoro, namely 5-p-fluorobenzoyl-6-chloro-1,2-dihydro-3H-pyrrolo[1,2-a]pyrrole-1-carboxylic acid and the pharmaceutically acceptable, non-toxic alkyl esters having from one to twelve carbon atoms and salts thereof.

7. The methyl ester of the compound of claim 6, namely methyl 5-p-fluorobenzyl-6-chloro-1,2-dihydro-3H-pyrrolo[1,2-a]pyrrole-1-carboxylate.

8. A compound of claim 3 in which Y is chloro and L is p-methylthio, namely 5-p-methylthiobenzoyl-6-chloro-1,2-dihydro-3H-pyrrolo[1,2-a]pyrrole-1-carboxylic acid and the pharmaceutically acceptable, non-toxic alkyl esters having from one to twelve carbon atoms and salts thereof.

9. The methyl ester of the compound of claim 8, namely methyl 5-p-methylthiobenzoyl-6-chloro-1,2-dihydro-3H-pyrrolo[1,2-a]pyrrole-1-carboxylate.

10. A compound of claim 3 in which Y is chloro and L is p-methoxy, namely 5-p-methoxybenzoyl-6-chloro-1,2-dihydro-3H-pyrrolo[1,2-a]pyrrole-1-carboxylic acid and the pharmaceutically acceptable, non-toxic alkyl esters having from one to twelve carbon atoms and salts thereof.

11. The methyl ester of the compound of claim 10, namely methyl 5-p-methoxybenzoyl-6-chloro-1,2-dihydro-3H-pyrrolo[1,2-a]pyrrole-1-carboxylate.

12. A compound of claim 3 in which Y is chloro and L is p-chloro, namely 5-p-chlorobenzoyl-6-chloro-1,2-dihydro-3H-pyrrolo[1,2-a]pyrrole-1-carboxylic acid and the pharmaceutically acceptable, non-toxic akyl esters having from one to twelve carbon atoms and salts thereof.

13. The methyl ester of the compound of claim 12, namely methyl 5-p-chlorobenzoyl-6-chloro-1,2-dihydro-3H-pyrrolo[1,2-a]pyrrole-1-carboxylate.

14. A compound of claim 2 in which Y is chloro and L is hydrogen, namely 5-benzoyl-6-chloro-1,2-dihydro-3H-pyrrolo[1,2-a]pyrrole-1-carboxylic acid and the pharmaceutically acceptable, non-toxic alkyl esters having from one to twelve carbon atoms and salts thereof.

15. The methyl ester of the compound of claim 4, namely methyl 5-benzoyl-6-chloro-1,2-dihydro-3H-pyrrolo[1,2-a]pyrrole-1-carboxylate.

16. A compound of claim 2 in which Y is chloro, and L is p-methylsulfonyl, namely 5-p-methylsulfonylbenzoyl-6-chloro-1,2-dihydro-3H-pyrrolo[1,2-a]pyrrole-1-carboxylic acid and the pharmaceutically acceptable, non-toxic alkyl esters having from one to twelve carbon atoms and salts thereof.

17. The methyl ester of the compound of claim 16, namely methyl 5-p-methylsulfonylbenzoyl-6-chloro-1,2-dihydro-3H-pyrrolo[1,2-a]pyrrole-1-carboxylate.

18. A compound of claim 3 in which Y is bromo and L is p-fluoro, namely 5-p-fluorobenzoyl-6-bromo-1,2-dihydro-3H-pyrrolo[1,2-a]pyrrole-1-carboxylic acid and the pharmaceutically acceptable, non-toxic alkyl esters having from one to twelve carbon atoms and salts thereof.

19. The methyl ester of the compound of claim 6, namely methyl 5-p-fluorobenzoyl-6-bromo-1,2-dihydro-3H-pyrrolo[1,2-a]pyrrole-1-carboxylate.

20. A compound of claim 2 in which Y is bromo and L is hydrogen, namely 5-benzoyl-6-bromo-1,2-dihydro-3H-pyrrolo[1,2-a]pyrrole-1-carboxylic acid and the pharmaceutically acceptable, non-toxic alkyl esters having from one to twelve carbon atoms and salts thereof.

21. The methyl ester of the compound of claim 4, namely methyl 5-benzoyl-6-bromo-1,2-dihydro-3H-pyrrolo[1,2-a]pyrrole-1-carboxylate.

22. A compound of claim 1 selected from the group in which Ar is

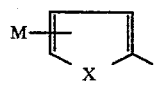

23. A compound of claim 22 in which X is oxygen.

24. A compound of claim 22 in which X is sulfur.

25. A compound of claim 24 wherein Y is chloro, and M is hydrogen, 5-(2-thenoyl)-6-chloro-1,2-dihydro-3H-pyrrolo[1,2-a]pyrrole-1-carboxylic acid and the pharmaceutically acceptable, non-toxic alkyl esters having from one to twelve carbon atoms and salts thereof.

26. A compound of claim 1 selected from the group in which Ar is

27. A compound of claim 1 selected from the group in which Ar is

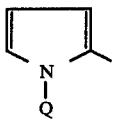

28. A composition for treating inflammation, pain or pyrexia in mammals consisting essentially of a pharmaceutically acceptable non-toxic excipient and a therapeutically effective amount of a compound of claim 1.

29. A method of treating inflammation, pain or pyrexia in mammals which comprises administering to a mammal suffering therefrom a therapeutically effective amount of a compound of claim 1.

30. A composition for administration to a pregnant mammal to delay onset of parturition consisting essentially of a pharmaceutically acceptable non-toxic excipient and a therapeutically effective amount of a compound of claim 1.

31. A method which comprises administering to a pregnant mammal to delay the onset of parturition a pharmaceutically effective amount of a compound of claim 1.

32. The method of claim 31 wherein said pregnant mammal is a woman who is not suffering from inflammation, pyrexia, or pain.

33. The method of claim 31 wherein said pregnant woman has had a previous spontaneous abortion, miscarriage or premature delivery, which occurred prior to the time for normal parturition at or about full term.

34. The method of claim 31 wherein said pregnant mammal is a woman who is not suffering from inflammation, pyrexia or nonparturition-causing pain but who is experiencing uterine muscle contractions, said compound being administered in a therapeutically effective amount adapted to reduce the intensity or duration of the uterine muscle contractions, stop the uterine muscle contractions altogether, whereby termination of the pregnancy is postponed from the time it otherwise would have happened.

* * * * *